United States Patent
Liew et al.

(12) 
(10) Patent No.: US 7,452,667 B2
(45) Date of Patent: Nov. 18, 2008

(54) DIAGNOSIS OF MILD OSTEOARTHRITIS BY DETERMINATION OF TNFAIP6 AND TGFBI RNA LEVELS

(75) Inventors: Choong-Chin Liew, Toronto (CA); K. Wayne Marshall, Toronto (CA); Hongwei Zhang, Toronto (CA)

(73) Assignee: Genenews, Inc., Richmond Hill, Ontario (CA)

( * ) Notice: Subject to any disclaimer, the term of this patent is extended or adjusted under 35 U.S.C. 154(b) by 581 days.

(21) Appl. No.: 10/661,242

(22) Filed: Sep. 12, 2003

(65) Prior Publication Data

US 2004/0209275 A1 Oct. 21, 2004

Related U.S. Application Data

(60) Provisional application No. 60/410,180, filed on Sep. 12, 2002.

(51) Int. Cl.
*C12Q 1/68* (2006.01)
*C07H 21/04* (2006.01)

(52) U.S. Cl. .................. 435/6; 536/23.5; 536/24.31

(58) Field of Classification Search ............... None
See application file for complete search history.

(56) References Cited

U.S. PATENT DOCUMENTS

2001/0051344 A1* 12/2001 Shalon et al. ................ 435/6

OTHER PUBLICATIONS

Kroese et al. Genetic tests and their evaluation: Can we answer the key questions? Genetics in Medicine. vol. 6, No. 6, pp. 475-480, 2004.*

Lucentini, J. Gene Association Studies Typically Wrong. vol. 18, No. 24, p. 20 (pp. 1/4 to 4/4), 2004.*

Marshall et al. Blood-based biomarkers for detecting mild osteoarthritis in the human knee. Osteoarthritis Cartilage. vol. 13, No. 10, pp. 861-871, Oct. 2005.*

Uchino et al. Growth Factor Expression in the Osteophytes of the Human Femoral Head in Osteoarthritis. Clinical Orthopaedics and Related Research. vol. 377, pp. 119-125, 2000.*

* cited by examiner

*Primary Examiner*—Daniel M. Sullivan
*Assistant Examiner*—Jennifer Dunston
(74) *Attorney, Agent, or Firm*—Edwards Angell Palmer & Dodge LLP; Kathleen Williams; Amy DeCloux

(57) ABSTRACT

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

1 Claim, No Drawings

SEQUENCE LISTING

```
<160> NUMBER OF SEQ ID NOS: 20

<210> SEQ ID NO 1
<211> LENGTH: 129
<212> TYPE: DNA
<213> ORGANISM: Human

<400> SEQUENCE: 1
gtttcttttt cctaaaacgg ttttatttaa ctcaatgtgt caaagttttt ttttaataat      60
cccaagaggg atgaagccgt gtccacaggg atatatacat cattatggtt cccatctttc     120
atacatgaa                                                             129

<210> SEQ ID NO 2
<211> LENGTH: 400
<212> TYPE: DNA
```

```
<213> ORGANISM: human
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t

<400> SEQUENCE: 2
aacaagctca gggctaccac tgncnctaca ttatgatcaa ctgcatgggg tcctacagga      60
gaagaccaag agacagagac agagaccagg gaaaatgacc gataccattc cttctcaggg    120
atgctacaca cccatggggc agaggatang aggttcctga aggcatcacc cctctggcca    180
tggctggtgt gcagacaaag ctggagattt ggagtagcct gttgtcccac tgactcttag    240
actgccccag ctaagaagaa ccaactcctc ctattacaga tgaaataaac aaagctactc    300
aagctctctg gcatcgccct gacggtcatc atgtgcttca catttccctc ctgccccccc    360
tgattttctg gaaagggag aaagngngtg aaaaaaaatg                            400

<210> SEQ ID NO 3
<211> LENGTH: 118
<212> TYPE: DNA
<213> ORGANISM: human

<400> SEQUENCE: 3
tatcccacgt actccaactt ccattcctcg ccctgccccc ggagccgagt cctgtatcag     60 cccctttatcc tcacacgctt ttctacaatg gcattcaata aagtgcacgt gtttctgg     118

<210> SEQ ID NO 4
<211> LENGTH: 359
<212> TYPE: DNA
<213> ORGANISM: Human

<400> SEQUENCE: 4
gctgaaatat cccttgggg actgcatatg ctgtacatgg ccacagcatc ggagcacgga      60
gacttccccg gaggtgctgc ctcagtgtgc gttgtcagca ttgtttagaa atgcaggatc    120
ctgtgtcagt ttctgaatgc cagtcacttc ccatttgctg ctccgctttt tggacactag    180
cactgacagg gttggaagag taaaattagg atacccctagg atccaccat ctttcaggtt    240 tgcttggtgc tggctgaaaa atgacttaat attctttctg gggcttgtca aagagtcctg    300
tccgttcttc tcctaagcca acccactta ccaggagtaa agccctagct gttgaagga     359

<210> SEQ ID NO 5
<211> LENGTH: 177
<212> TYPE: DNA
<213> ORGANISM: human
<220> FEATURE:
<221> NAME/KEY: misc_feature
<222> LOCATION: (168)..(168)
<223> OTHER INFORMATION: n is a, c, g, or t
```

<400> SEQUENCE: 5

```
ctcctccagc gcccgcagca cccaccccgc accggcgact ccatcttcat ggccacccc     60
tgcggtggac ggttgaccac cagccaccac atcatcccag agctgagctc ctccagcggg   120
atgacgccgt ccccaccacc tccctcttct tcttttcat ccttctgnct ctttggt       177
```

<210> SEQ ID NO 6
<211> LENGTH: 500
<212> TYPE: DNA
<213> ORGANISM: Human
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t

<400> SEQUENCE: 6

```
aaccgatnnc agagaaaatt ttgcatgcaa aaatttagga agatgaatga tactcattat    60
tattattctt tcagtccctg gctatcttct tcagtgactg ctccatccat ggtagcccca   120
gtcactttg catctattgt agaagaagaa ctacaacaag aagcagctct tattagaagt    180
cgagaaaaac cgttggctct gattcagatt gaggagcatg ccatacaaga tttattggtt   240
ttctatgagg catttggcaa ccctgaagag tttgcattgt tgaaaggaca ccgcagggac   300
cactggcagt acctatgtgg aataagcatg gatgctagtt cactgtggag ttgagatgca   360
ttttacataa ttatgagttt ggtcatataa agaaaagctg tggaaaaaga gtcttagaga   420
ttttgtaata tcattctaaa tagattaaga aaagatataa tttctttact gcagtaaatc   480
atataatgtt tgnatgatta                                                500
```

<210> SEQ ID NO 7
<211> LENGTH: 459
<212> TYPE: DNA
<213> ORGANISM: human

<400> SEQUENCE: 7

```
tcaatagacc gggatgttaa aaacatatag caaaaatctg aagaaaatgt gctaagctat    60
aaaagagata acttctgggg aaggaagtag agtggaagga tgatgaacct agtggggacc   120
cagaggagac actgtatctc tgtccaaaga aattgctatg attacacgtt tgtcccctcc   180
aaaactcatg ctgaaacttg gtcccagtg tagcagtgtt aggagatggg ctgatgagag    240
gtgattgaat catggagctc tcatgaatgt tttattgtca ttattgaggg agtgggatgt   300
tgtaaaggga gccaagccca ttgtgctttc cctctttagt actcactccc ttgctcttct   360
gcgatggaat gacacagcac aaaggtcctc accatatgcc aaccctcaa ccttggattt    420
cccagcatcc agaaccatga actattcttt ataaattac                          459
```

<210> SEQ ID NO 8
<211> LENGTH: 470
<212> TYPE: DNA
<213> ORGANISM: human
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (200)..(200)

<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 8
acacactctt catctgaagc ttcactgaag gtgatcatct gcagaccang ggtcatgatg      60
ttcctgctga ggagtcttct gctgctttct attgtgttct ccatggaggg tgcagatgag     120
gagcgactta gctgtgaaag aggctggagc aggtctggct ctcgctgctt caggtttttc     180
tccaggtctg tgaactgggn cacagnagga gagaaactgt cagagtcttg gagggaatct     240
ggcttctgtg catgatcaag tggagaatga ctttctgctg agtctggtgc cgggctccac     300
acgctgctgg attggaggtc atgatggaga acaagatgga cagtggntgt gggctgatgg     360
atctgtgtat ggntacacca actggngctc aggagagcct agnggcgggg tctgagcact     420
gcttggagat caactggaca tcgaaccgnt gctggaatga tcagcgctgg                470

<210> SEQ ID NO 9
<211> LENGTH: 304
<212> TYPE: DNA
<213> ORGANISM: Human
<220> FEATURE:
<221> NAME/KEY: misc_feature
<222> LOCATION: (202)..(202)
<223> OTHER INFORMATION: n is a, c, g, or t

<400> SEQUENCE: 9
tccaaaaata ggtcattctt ttattttcta aagtatctaa actgtactaa cattcagtgt      60
tgtgtttcat tctaaatttg cagctgaaat aaatttattt gcgatagcag aaatatctta     120
ttattcatcc tcagaaataa aggatttgaa gggatagaga ttatatgata aatttataga     180
agactttcag aatttgaatg cnttttgttt agtgctatga aatgacaata gaaaaaagtc     240
tcgacttcaa ttaaaagtta cacaaacaaa caaatctaca ggcatgtctt tatataccat     300
cagg                                                                  304

<210> SEQ ID NO 10
<211> LENGTH: 424
<212> TYPE: DNA
<213> ORGANISM: human
<220> FEATURE:
<221> NAME/KEY: misc_feature
<222> LOCATION: (420)..(420)
<223> OTHER INFORMATION: n is a, c, g, or t

<400> SEQUENCE: 10

```
gagctgcttt tatgctgaaa atggtcattt ccctgttcac ttactgacat gtgaagaagg      60
gtttcttgct ttcttaaaca tttccgtaag gcaggctaga aatgtaatac ttcaaatgtt     120
tgatgattat ggtcttttga taggaataga ttctgcttgg gatatatatc caggcactct     180
ctaaggtcta gggttgatat taacaaagga atgtacttag aatagcagta cattttatgc     240
aaatatggaa attattttaa gaaacaatga catatcaaaa ctgcttttta catgattttg     300
aaatagacta gaaagctttc cctatagaca tattaatatt ccaatcataa ctttaattca     360
agaatgcagt tttaccaaaa gaaaaatttg aaaatttcta ttcaggctac tggaattggn     420
tatg                                                                  424
```

<210> SEQ ID NO 11
<211> LENGTH: 105
<212> TYPE: DNA
<213> ORGANISM: human
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 11

```
cacaagctta cctgctgccc cccggggcgc tnctgagatt gtaatatctt ttgaccttga      60
ggccttgggg cnactgaatg nctctgcggc ggtcctgagg acggg                    105
```

<210> SEQ ID NO 12
<211> LENGTH: 214
<212> TYPE: DNA
<213> ORGANISM: human

<400> SEQUENCE: 12

```
gttattctct agaaaatagt atttaaagac attttatgaa atcttcattg tcaaaacctt      60
taataaaagt ggaaatattt tgaaatgcct ttttcttgat acactcatcc acgtgttgct     120
gattgtccac atttcatgat aaatgagagc tctgcagaga atgttagcct gtctgttgta     180
attgtaatct tcaggtaggc acttctttgt taag                                214
```

<210> SEQ ID NO 13
<211> LENGTH: 500
<212> TYPE: DNA
<213> ORGANISM: human

<400> SEQUENCE: 13

```
tcttggccta cgtgaatcac catgtaattg cattcattgc catggtttta aaggtccgct      60
atgtgctgac gatgtccaca cctgtttcct gaattcacac agccagctcc ctgcttagca     120 tctcccttg aagatctcag gaaaatctga aactcaacat gttcaaggca gaactcctga     180
tctcaccctc atgtaaaatc tgtcccaacc taggttcctc catgtcaata gtggtgtaac     240
catccacctg cccctttgtcc taaacatcca acacatcagc aagtcctgcc gtatcaagtt     300
cctgcattta tctctaatct ttgtggccac tacctaggtt taggccatta tcacctctgg     360
cctggattgt gcaatagctt cctatctagt caccctacct ccactcctgt ctctcccaat     420
```

-continued

```
ccattctcac agagcaatga atgtgatcct ttcataatga gaactgcttc gtatcaatta      480
tctgcctaaa ccttctaatg                                                  500
```

<210> SEQ ID NO 14
<211> LENGTH: 577
<212> TYPE: DNA
<213> ORGANISM: human

<400> SEQUENCE: 14

```
ctcgattttt aagaggtatt taactcttta cttgcactga gaatggcaaa tctccctgtt       60
ctatcacccg cctgtccact gggctcaccg tatctgtaca acgcttggct tcctgtctca      120
ctgcagctgt gtgcctgtct cccctgactt tggggtctgt gtgggtcagg cggtcccttc      180
cagctctcgg ccacaggtac tgtctcttca agagtgttct aacactgctg ctccaccgaa      240
aacattcaag tccttcatcc ctctggactc cgccatggtc aggcgtggga gcagcactcc      300
aagcccctcc tctcactcgt ggagcacaag gtgtgcggca cattcatgac agaaaggccc      360
tccagttact gcgacagcca acctttgtaa catgcgaaat ccccatgggt gccgggctat      420
ctgccccgac accaacagca cccttatgca gtttggggg ttcccatggc tcatagtggg       480
gcacactccc acccgcaaca cttagcatca tgatggcggc cttcatcagg acgtccacac      540
tgcaaggaca ttggcaccac cttacccaac cgtgtgt                              577
```

<210> SEQ ID NO 15
<211> LENGTH: 294
<212> TYPE: DNA
<213> ORGANISM: human
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t

<400> SEQUENCE: 15

```
aagcagtgaa gtgtgtggan gcancagcag gtacttaact ttgaccgaac gctagccaag       60
tgcattataa ggtgattgan gatgaattgt nccttaatct ccatccttct tccatctgca      120
```

```
actgatacta tgcggncctt tagtgctgat catatttctg ntctaaatac tnggcgcaca      180
ataggtactc agnaacagtt ctttgattgg gtgaatggat gagtgaatga agacagaaga      240
caggctttaa actttttttaa agtatggttt agaagaaaaa ggagngtagt tttg           294
```

<210> SEQ ID NO 16
<211> LENGTH: 400
<212> TYPE: DNA
<213> ORGANISM: human
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 16

```
ctgtancaga gaaccaagaa ccntctgaag gaacntttta cnaaatatat aactcttact      60
aacaatgtag nacaatttgg ggaagaagna tgnaatctca aagaaagtgc naactactca     120
tttgttaact tgtgtagaaa cttctgttat tcaacgtagt cctttattc cgaaatggat      180 aagcattaaa agagattngt cttaatttac tttcaaaaac ttctttaatt agcataaaga     240
aaggaaagaa gaataagagt ttctggcttt aagttaattt ttcacatgga gaatatatgt     300
ataaatacag tatcatgtta atagatactg gtaaagtgtc tgaggtttca tcaaaaggga     360
aagaaagcaa ttgtgctaga tataaatcag ggaaggattc                            400
```

<210> SEQ ID NO 17
<211> LENGTH: 100
<212> TYPE: DNA
<213> ORGANISM: Human
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:

```
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (56)..(58)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t

<400> SEQUENCE: 17
aaaatgtccg tgaaaatgag anctangcat nactttngcc aaagtaaggc ctttgnnnta    60
tatttatata ggccatacat agagaantca cctagctnta                        100

<210> SEQ ID NO 18
<211> LENGTH: 109
<212> TYPE: DNA
<213> ORGANISM: human
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t

<400> SEQUENCE: 18
cccctcaggg tcngacacta gtggatccaa agnaattcgg acaggnctgg catnaccctg    60
ccaaaggtga tggggtcgcc tacacatgtg tatgtcactg tgagnggat              109

<210> SEQ ID NO 19
<211> LENGTH: 31
<212> TYPE: DNA
<213> ORGANISM: Artificial sequence
<220> FEATURE:
<223> OTHER INFORMATION: primer

<400> SEQUENCE: 19
gccaagctcg aaattaaccc tcactaaagg g                                   31

<210> SEQ ID NO 20
<211> LENGTH: 33
<212> TYPE: DNA
<213> ORGANISM: Artificial sequence
<220> FEATURE:
```

```
<223> OTHER INFORMATION: primer

<400> SEQUENCE: 20
ccagtgaatt gtaatacgac tcactatagg gcg                                          33
```

DIAGNOSIS OF MILD OSTEOARTHRITIS BY DETERMINATION OF TNFAIP6 AND TGFBI RNA LEVELS

RELATED APPLICATION(S)

This application claims the benefit of U.S. Provisional Application No. 60/410,180 filed on Sep. 12, 2002. The entire teachings of the above application are incorporated herein by reference.

FIELD OF THE INVENTION

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

BACKGROUND

Osteoarthritis (OA) is a chronic disease in which the articular cartilage that lies on the ends of bones that forms the articulating surface of the joints gradually degenerates over time. There are many factors that are believed to predispose a patient to osteoarthritis including genetic susceptibility, obesity, accidental or athletic trauma, surgery, drugs and heavy physical demands. Osteoarthritis is initiated by damage to the cartilage of joints. The two most common injuries to joints are sports-related injuries and long term "repetitive use" joint injuries. Joints most commonly affected by osteoarthritis are the knees, hips and hands. In most cases, due to the essential weight-bearing function of the knees and hips, osteoarthritis in these joints causes much more disability than osteoarthritis of the hands. As cartilage degeneration progresses, secondary changes occur in other tissues in and around joints including bone, muscle, ligaments, menisci and synovium. The net effect of the primary failure of cartilage tissue and secondary damage to other tissues is that the patient experiences pain, swelling, weakness and loss of functional ability in the afflicted joint(s). These symptoms frequently progress to the point that they have a significant impact in terms of lost productivity and or quality of life consequences for the patient.

Articular cartilage is predominantly composed of chondrocytes, type II collagen, proteoglycans and water. Articular cartilage has no blood or nerve supply and chondrocytes are the only type of cell in this tissue. Chondrocytes are responsible for manufacturing the type II collagen and proteoglycans that form the cartilage matrix. This matrix in turn has physical-chemical properties that allow for saturation of the matrix with water. The net effect of this structural-functional relationship is that articular cartilage has exceptional wear characteristics and allows for almost frictionless movement between the articulating cartilage surfaces. In the absence of osteoarthritis, articular cartilage often provides a lifetime of pain-free weight bearing and unrestricted joint motion even under demanding physical conditions.

During fetal development, articular cartilage is initially derived from the interzone of mesenchymal condensations. The mesenchymal cells cluster together and synthesize matrix proteins. The tissue is recognized as cartilage when the accumulation of matrix separates the cells, which are spherical in shape and are now called chondrocytes. During cartilage formation and growth, chondrocytes proliferate rapidly and synthesize large volumes of matrix. Prior to skeletal maturity, chondrocytes are at their highest level of metabolic activity. As skeletal maturation is reached, the rate of chondrocyte metabolic activity and cell division declines. After completion of skeletal growth, most chondrocytes do not divide but do continue to synthesize matrix proteins such as collagens, proteoglycans and other noncollagenous proteins. (Zaleske D J. Cartilage and Bone Development. Instr Course Lect 1998;47:461-); (Buckwalter J A, Mankin H J. Articular Cartilage: Tissue Design and Chondrocyte-Matrix Interactions. Instr Course Lect 1998;47:477-86.)

Like all living tissues, articular cartilage is continually undergoing a process of renewal in which "old" cells and matrix components are being removed (catabolic activity) and "new" cells and molecules are being produced (anabolic activity). Relative to most tissues, the rate of anabolic/catabolic turnover in articular cartilage is low. Long-term maintenance of the structural integrity of mature cartilage relies on the proper balance between matrix synthesis and degradation. Chondrocytes maintain matrix equilibrium by responding to chemical and mechanical stimuli from their environment. Appropriate and effective chondrocyte responses to these stimuli are essential for cartilage homeostasis. Disruption of homeostasis through either inadequate anabolic activity or excessive catabolic activity can result in cartilage degradation and osteoarthritis. (Westacott C I, Sharif M. Cytokines in Osteoarthritis: Mediators or Markers of Joint Destruction? Semin Arthritis Rheum 1996;25:254-72). Most tissues that are damaged and have increased catabolic activity are able to mount an increased anabolic response that allows for tissue healing. Unfortunately, chondrocytes have very limited ability to up-regulate their anabolic activity and increase the synthesis of proteoglycan and type II collagen in response to damage or loss of cartilage matrix. This fundamental limitation of chondrocytes is the core problem that has precluded the development of therapies that can prevent and cure osteoarthritis. Additionally, there is a need for a definitive diagnostic test for detecting early osteoarthritis, and a prognostic test that effectively monitors a patient's response to therapy.

Joint pain is the most common manifestation of early osteoarthritis. The pain tends to be episodic lasting days to weeks and remitting spontaneously. Although redness and swelling of joints is uncommon, joints become tender during a flare-up of osteoarthritis.

"Mild" or "early stage osteoarthritis" is difficult to diagnose. The physician relies primarily on the patient's history and physical exam to make the diagnosis of mild osteoarthritis. X-rays do not show the underlying early changes in articular cartilage. There are no recognized biochemical markers used to confirm the diagnosis of early stage osteoarthritis.

X-ray changes confirm the diagnosis of moderate osteoarthritis. X-rays of normal joints reveal well preserved symmetrical joint spaces. Changes seen on the x-rays of patients with osteoarthritis include new bone formation (osteophytes), joint space narrowing and sclerosis (bone thickening). There are no recognized biochemical markers used to confirm the diagnosis of "moderate osteoarthritis" at this stage.

The clinical exam of a joint with severe osteoarthritis reveals tenderness, joint deformity and a loss of mobility. Passive joint movement during examination may elicit crepitus or the grinding of bone-on-bone as the joint moves. X-ray changes are often profound: the joint space may be obliterated and misalignment of the joint can be seen. New bone formation (osteophytes) is prominent. Again, there are no recognized biochemical markers used to confirm the diagnosis of "severe osteoarthritis".

"Osteoarthritis" is the most common chronic joint disease. It is characterized by progressive degeneration and eventual loss of cartilage. Currently, there is a need for an effective therapy that will alter the course of osteoarthritis. Further advances in preventing, modifying or curing the osteoarthritic disease process critically depends, at least in part, on a thorough understanding of the molecular mechanisms underlying anabolic and catabolic processes in cartilage. Since cellular functions are substantially determined by the genes that the cells express, elucidating the genes expressed in articular cartilage at different developmental and disease stages will inevitably provide new insights into the molecules and mechanisms involved in cartilage formation, injury, disease and repair.

cDNA libraries from putatively normal and severely osteoarthritic human cartilage tissue have been constructed (Kumar et al., 46th Annual Meeting, Orthopaedic Res. Soc., Abstract, p. 1031). However, this work does not adequately address the differentiation of chondrocyte gene expression from differing severities of osteoarthritic human cartilage (mild, moderate, marked and severe). In addition, the "normal cartilage" samples were obtained from deceased donors more than 24 hours after death. Thus, this cDNA library does not truly reflect normal chondrocyte gene expression due to the rapid degeneration of RNA that occurs after cessation of perfusion to the sampled joint, as demonstrated by baboon studies, presented herein below.

Even upon construction of cDNA libraries from individuals demonstrating differing severities of osteoarthritis, it has been difficult to identify sequences which will be particularly useful in the diagnosis of osteoarthritis. More importantly previous studies have not identified sequences which will be either effective in diagnosing the degree of advancement of osteoarthritis so as to aid in both early detection and treatment, or in identifying novel therapeutic targets.

Even upon construction of cDNA libraries from individuals demonstrating differing severities of osteoarthritis, it has been difficult to identify sequences which will be particularly useful in the diagnosis of osteoarthritis. More importantly previous studies have not identified sequences which will be effective in diagnosing the degree of advancement of osteoarthritis so as to aid in both early detection, and treatment. Additionally previous studies have not identified sequences which will be effective in identifying agents which will be useful in treating osteoarthritis.

SUMMARY OF THE INVENTION

The invention relates to the identification and selection of sequences which demonstrate particular advantage in identifying individuals having osteoarthritis (OA). The invention also provides a selection of sequences particularly useful in diagnosing the degree of advancement of osteoarthritis of an individual and in the identification of novel therapeutic targets for OA. The invention further provides for the use of these sequences as a tool to diagnose disease progression and to monitor the efficacy of therapeutic regimens.

In one embodiment, the invention provides for an isolated biomarker comprising 51% or more genes selected from the group consisting of the nucleic acids identified in Tables 1, 3, 5, 6a and 7a.

In one embodiment, the invention provides for an isolated biomarker comprising two or more genes selected from the group consisting of the nucleic acids identified in Tables 1, 3, 5, 6a and 7a.

In one embodiment, the invention provides for an isolated biomarker consisting essentially of the nucleic acids identified in Tables 1, 3, 5, 6a and 7a.

In one embodiment, the invention provides for an isolated biomarker comprising 51% or more genes selected from the group consisting of the nucleic acids identified in Table 6b.

In one embodiment, the invention provides for an isolated biomarker comprising two or more genes selected from the group consisting of the nucleic acids identified in Table 6b.

In one embodiment, the invention provides for an isolated biomarker consisting essentially of the nucleic acids identified in Table 6b.

In one embodiment, the invention provides for an isolated biomarker comprising 51% or more genes selected from the group consisting of the nucleic acids identified in Table 6c.

In one embodiment, the invention provides for an isolated biomarker comprising two or more genes selected from the group consisting of the nucleic acids identified in Table 6c.

In one embodiment, the invention provides for an isolated biomarker consisting essentially of the nucleic acids identified in Table 6c.

In one embodiment, the invention provides for an isolated biomarker comprising 51% or more genes selected from the group consisting of the nucleic acids identified in Tables 2, 4, 5, 6d and 7b.

In one embodiment, the invention provides for an isolated biomarker comprising two or more genes selected from the group consisting of the nucleic acids identified in Tables 2, 4, 5, 6d and 7b.

In one embodiment, the invention provides for an isolated biomarker consisting essentially of the nucleic acids identified in Tables 2, 4, 5, 6d and 7b.

In another embodiment, the invention teaches a method of diagnosing mild osteoarthritis in an individual, comprising determining the level of expression of a biomarker in a sample where the biomarker comprises one or more polynucleotide sequences selected from the group consisting of the nucleic acids identified in Tables 1, 3, 5, 6a, 7a, whereby a difference in the level of expression of the biomarker compared to a biomarker control is indicative or predictive of mild osteoarthritis.

In yet another embodiment, the polynucleotide sequences are from the 5' region of a gene selected from the group consisting of the nucleic acids identified in Tables 1, 3, 5, 6a, 7a.

In yet another embodiment, the polynucleotide sequences are from the 3' region of a gene selected from the group consisting of the nucleic acids identified in Tables 1, 3, 5, 6a, 7a.

In yet another embodiment, the polynucleotide sequences are from the internal coding region of a gene selected from the group consisting of the nucleic acids identified in Tables 1, 3, 5, 6a, 7a.

In another embodiment, the invention teaches a method of diagnosing severe osteoarthritis in an individual, comprising determining the level of expression of a biomarker in a sample where the biomarker comprises one or more polynucleotide sequences selected from the group consisting of the nucleic acids identified in Tables 2, 4, 5, 6d, 7b whereby a difference in the level of expression of the biomarker compared to a biomarker control is indicative or predictive of severe osteoarthritis.

In yet another embodiment, the polynucleotide sequences are from the 5' region of a gene selected from the group consisting of the nucleic acids identified in Tables 2, 4, 5, 6d, 7b.

In yet another embodiment, the polynucleotide sequences are from the 3' region of a gene selected from the group consisting of the nucleic acids identified in Tables 2, 4, 5, 6d, 7b.

In yet another embodiment, the polynucleotide sequences are from the internal coding region of a gene selected from the group consisting of the nucleic acids identified in Tables 2, 4, 5, 6d, 7b.

In another embodiment, the invention teaches a method of diagnosing moderate osteoarthritis in an individual, comprising determining the level of expression of a biomarker in a sample where the biomarker comprises one or more polynucleotide sequences selected from the group consisting of the nucleic acids identified in Table 6b, whereby a difference in the level of expression of the biomarker compared to a biomarker control is indicative or predictive of moderate osteoarthritis.

In yet another embodiment, the polynucleotide sequences are from the 5' region of a gene selected from the group consisting of the nucleic acids identified in Table 6b.

In yet another embodiment, the polynucleotide sequences are from the 3' region of a gene selected from the group consisting of the nucleic acids identified in Table 6b.

In yet another embodiment, the polynucleotide sequences are from the internal coding region of a gene selected from the group consisting of the nucleic acids identified in Table 6b.

In another embodiment, the invention teaches a method of diagnosing marked osteoarthritis in an individual, comprising determining the level of expression of a biomarker in a sample where the biomarker comprises one or more polynucleotide sequences selected from the group consisting of the nucleic acids identified in Table 6c, whereby a difference in the level of expression of the biomarker compared to a biomarker control is indicative or predictive of marked osteoarthritis.

In yet another embodiment, the polynucleotide sequences are from the 5' region of a gene selected from the group consisting of the nucleic acids identified in Table 6c.

In yet another embodiment, the polynucleotide sequences are from the 3' region of a gene selected from the group consisting of the nucleic acids identified in Table 6c.

In yet another embodiment, the polynucleotide sequences are from the internal coding region of a gene selected from the group consisting of the nucleic acids identified in Table 6c.

In another embodiment, the invention teaches a method for monitoring efficacy of a drug for treatment of mild osteoarthritis in a patient, comprising the steps of obtaining a sample from a patient before treatment and a second sample from the patient after treatment; detecting the level of expression of an isolated biomarker comprising two or more genes selected from the group consisting of the nucleic acids identified in Tables 1, 3, 5, 6a and 7a. in the first sample and the second sample; and determining a difference in the level of expression of the biomarker in the first sample as compared with the second sample, where the difference in the level of expression is indicative of the efficacy of the drug for treatment of mild osteoarthritis in the patient.

In another embodiment, the invention teaches a method for monitoring efficacy of a drug for treatment of moderate osteoarthritis in a patient, comprising the steps of obtaining a sample from a patient before treatment and a second sample from the patient after treatment; detecting the level of expression of an isolated biomarker comprising two or more genes selected from the group consisting of the nucleic acids identified in Table 6b in the first sample and the second sample; and determining a difference in the level of expression of the biomarker in the first sample as compared with the second sample, where the difference in the level of expression is indicative of the efficacy of the drug for treatment of moderate osteoarthritis in the patient.

In another embodiment, the invention teaches a method for monitoring efficacy of a drug for treatment of marked osteoarthritis in a patient, comprising the steps of obtaining a sample from a patient before treatment and a second sample from the patient after treatment; detecting the level of expression of an isolated biomarker comprising two or more genes selected from the group consisting of the nucleic acids identified in Table 6c in the first sample and the second sample; and determining a difference in the level of expression of the biomarker in the first sample as compared with the second sample, where the difference in the level of expression is indicative of the efficacy of the drug for treatment of marked osteoarthritis in the patient.

In another embodiment, the invention teaches a method for monitoring efficacy of a drug for treatment of severe osteoarthritis in a patient, comprising the steps of obtaining a sample from a patient before treatment and a second sample from the patient after treatment; detecting the level of expression of an isolated biomarker comprising two or more genes selected from the group consisting of the nucleic acids identified in Tables 2, 4, 5, 6d and 7b in the first sample and the second sample; and determining a difference in the level of expression of the biomarker in the first sample as compared with the second sample, where the difference in the level of expression is indicative of the efficacy of the drug for treatment of severe osteoarthritis in the patient.

In another embodiment, the invention teaches a method of identifying a therapeutic agent for the treatment of osteoarthritis, the method comprising providing a sample from a patient diagnosed with osteoarthrtis, measuring the level of expression of a biomarker as set out in Tables 1-7 in the presence and the absence of the therapeutic agent; and comparing the level of expression measured in the presence of the therapeutic agent to the level of expression measured in the absence of the therapeutic agent, wherein a decrease in the differential expression of the biomarker is indicative of a therapeutic agent for the treatment of osteoarthritis.

In another embodiment, the sample is human cartilage.

In another embodiment, the biomarker is immobilized to a microarray.

In another embodiment, the level of expression of the biomarker is determined by hybridization to a microarray or real time RT-PCR.

In another embodiment, the invention provides for a kit comprising an isolated biomarker of one or more of the subject isolated biomarkers described above and packaging means therefore.

In another embodiment, the invention provides for a microarray comprising an isolated biomarker of one or more of the subject isolated biomarkers, described above, bound to a solid support.

DETAILED DESCRIPTION

The invention relates to methods of profiling gene sequences expressed in human chondrocytes to identify differential gene expression in chondrocytes at different stages of disease progression. Differentially expressed genes and their products (e.g., mRNAs and proteins) can be used in methods for diagnosis, prognosis, screening, or treatment of osteoarthritis.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995).

Definitions

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entireties.

The following definitions are provided for specific terms which are used in the following written description.

As used herein, "osteoarthritis" refers to a particular form of arthritis, and in particular a chronic disease in which the articular cartilage that lies on the ends of bones that form the articulating surface of the joints gradually degenerates over time. Cartilage degeneration can be caused by an imbalanced catabolic activity (removal of "old" cells and matrix components) and anabolic activity (production of "new" cells and molecules) (Westacott et al., 1996, *Semin Arthritis Rheum*, 25:254-72).

As used herein, "cartilage" or "articular cartilage" refers to elastic, translucent connective tissue in mammals, including human and other species. Cartilage is composed predominantly of chondrocytes, type II collagen, small amounts of other collagen types, other noncollagenous proteins, proteoglycans and water, and is usually surrounded by a perichondrium, made up of fibroblasts, in a matrix of type I and type II collagen as well as other proteoglycans. Although most cartilage becomes bone upon maturation, some cartilage remains in its original form in locations such as the nose, ears, knees, and other joints. The cartilage has no blood or nerve supply and chondrocytes are the only type of cell in this tissue.

As used herein, "chondrocyte" refers to cells from cartilage.

As used herein, "synovial fluid" refers to fluid secreted from the "synovial sac" which surrounds each joint. Synovial fluid serves to protect the joint, lubricate the joint and provide nourishment to the articular cartilage. Synovial fluid useful according to the invention contains cells from which RNA can be isolated according to methods well known in the art as described herein.

As used herein, the term "osteoarthritis (OA) staging" or "osteoarthritis (OA) grading" refers to determining the onset and or the degree of advancement or progression of the disease in the cartilage. In order to classify cartilage into different disease stages, a scoring system is used according to known methods in the art. Preferably the scoring system described in Marshall (Marshall W., 1996, *The Journal of Rheumatology*, 23:582-584, incorporated by reference) is used. According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A scoring system is then applied in which each articular surface receives an OA severity number value that reflects the cartilage severity grade for that surface. For example, if the medial femoral condyle has a grade I lesion as its most severe cartilage damage a value of 1 is assigned. A total score for the patient is then derived from the sum of the scores on the 6 articular surfaces. Based on the total score, each patient is placed into one of 4 OA groups: "mild" (early) is defined as having a Marshall score of 1-6, "moderate" is defined as having a Marshall score of 7-12, "marked" is defined as having a Marshall score of 13-18 and "severe" is defined as having a Marshall score of greater than 18.

As used herein, "diagnosis" refers to a process of determining if an individual is afflicted with a disease or ailment. "Diagnosis of OA" or "OA diagnosis", according to the invention, means determining if an individual is afflicted with OA, or, once a patient is diagnosed as having OA, determining the OA stage or grade based on the medical history and physical examination of the patient using methods known in the art (i.e., joint X ray). Preferably, OA stages are measured using the scoring system described by Marshall, supra. "Prognosis of OA" refers to a prediction of the probable occurrence and/or progression of OA in a patient, as well as the likelihood of recovery from OA, or the likelihood of ameliorating symptoms of OA or the likelihood of reversing the effects of OA.

As used herein, "patient" refers to a mammal who is diagnosed with arthritis and further includes a mammal who is diagnosed with the mild, moderate, marked, or severe form of OA.

As used herein, "normal" refers to an individual or group of individuals who have not shown any OA symptoms, including joint pain, and have not been diagnosed with cartilage injury or OA. Preferably said normal individual(s) is not on medication affecting OA and has not been diagnosed with any other disease. More preferably normal individuals have similar sex, age and body mass index (BMI) as compared with the test samples. "Normal", according to the invention, also refers to a samples isolated from normal individuals and includes total RNA or mRNA isolated from normal individuals. A sample taken from a normal individual can include RNA isolated from a cartilage tissue sample wherein RNA is isolated from a whole or a piece of cartilage isolated from cartilage tissue from an individual who was not diagnosed with OA and does not show any symptoms of OA at the time of tissue removal. In one embodiment of the invention, the "normal" cartilage sample is isolated at 14 hours post-mortem and the integrity of mRNA samples extracted is confirmed. A sample taken from a normal individual can also include RNA isolated from a sample wherein the sample is from an individual who has not been diagnosed with OA and does not show any symptoms of OA at the time the sampl is isolated.

As used herein, the term "biomarker" refers to a set of genes that are differentially regulated during the course of a disease.

As used herein, "isolated biomarker" means that the biomarker is isolated from and therefore not part of a mixture containing a set of OA genes including those taught in WO 02/070737, of more than 50 genes.

The term "comprising" means including the recited sequences, i.e. the "biomarker" sequences, and also including unrecited sequences.

The term "consisting of" means that only those sequences recited are present in the biomarker and no other sequences are present in the biomarker.

The term "consisting essentially of" means that the recited sequences are present in the biomarker, i.e. OA stage-specific sequences. The term "consisting essentially of" means that additional unrecited sequences which are OA-specific are not present in the biomarker. Thus "consisting essentially of" does not exclude sequences which are not OA-specific. OA-specific or stage-specific OA, as defined herein, means that a given sequence is differentially expressed in mild, moderate, marked, and/or severe OA relative to normal (not afflicted with OA).

In one embodiment, a biomarker for the diagnosis of osteoarthritis consists essentially of the genes as set out in Tables 1-7.

In another embodiment, a biomarker for the diagnosis of mild osteoarthritis consists essentially of the genes disclosed in Tables 1, 3, 5, 6a or 7a.

In another embodiment, a biomarker for the diagnosis of severe osteoarthritis consists essentially of the genes as set out in Tables 2, 4, 5, 6d or 7b.

In another embodiment, a biomarker for the diagnosis of moderate osteoarthritis consists essentially of the genes disclosed in Table 6b.

In another embodiment, a biomarker for the diagnosis of marked osteoarthritis consists essentially of the genes disclosed in Table 6c.

A "gene", as used herein, refers to DNA encoding mRNA and does not include promoters and enhancers upstream of the coding region.

As used herein, "polypeptide sequences encoded by" refers to the amino acid sequences obtained after translation of the protein coding region of a gene, as defined herein. The mRNA nucleotide sequence for each gene is identified by its GENBANK Accession number (see Tables 1-7) and the corresponding polypeptide sequence is identified by a Protein Accession Number or GefSeq or RefSeq (see Tables 1-7). The GENBANK Accession numbers identified in Tables 1-7 provide the location of the 5' UTR, protein coding region (CDS) and 3' UTR within the mRNA nucleotide sequence of each gene.

When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand. "Antigenic fragments" may be 5000, 1000, 500, 400, 300, 200, 100, 50 or 25 or 20 or 10 or 5 amino acids in length.

As used herein, the "5' end" refers to the end of an mRNA up to the first 1000 nucleotides or ⅓ of the mRNA (where the full length of the mRNA does not include the poly A tail), starting at the first nucleotide of the mRNA. The "5' region" of a gene refers to a polynucleotide (double-stranded or single-stranded) located within or at the 5' end of a gene, and includes, but is not limited to, the 5' untranslated region, if that is present, and the 5' protein coding region of a gene. The 5' region is not shorter than 8 nucleotides in length and not longer than 1000 nucleotides in length. Other possible lengths of the 5' region include but are not limited to 10, 20, 25, 50, 100, 200, 400, and 500 nucleotides.

As used herein, the "3' end" refers to the end of an mRNA up to the last 1000 nucleotides or ⅓ of the mRNA, where the 3' terminal nucleotide is that terminal nucleotide of the coding or untranslated region that adjoins the poly-A tail, if one is present. That is, the 3' end of an mRNA does not include the poly-A tail, if one is present. The "3' region" of a gene refers to a polynucleotide (double-stranded or single-stranded) located within or at the 3' end of a gene, and includes, but is not limited to, the 3' untranslated region, if that is present, and the 3' protein coding region of a gene. The 3' region is not shorter than 8 nucleotides in length and not longer than 1000 nucleotides in length. Other possible lengths of the 3' region include but are not limited to 10, 20, 25, 50, 100, 200, 400, and 500 nucleotides.

As used herein, the "internal coding region" of a gene refers to a polynucleotide (double-stranded or single-stranded) located between the 5' region and the 3' region of a gene as defined herein. The "internal coding region" is not shorter than 8 nucleotides in length and not longer than 1000 nucleotides in length. Other possible lengths of the "internal coding region" include but are not limited to 10, 20, 25, 50, 100, 200, 400, and 500 nucleotides.

The 5', 3' and internal regions are non-overlapping and may, but need not be contiguous, and may, but need not, add up to the full length of the corresponding gene.

As used herein, the "amino terminal" region of a polypeptide refers to the polypeptide sequences encoded by polynucleotide sequences (double-stranded or single-stranded) located within or at the 5' end of a gene, and includes, but is not limited to, the 5' protein coding region of a gene. As used herein, the "amino terminal" region refers to the amino terminal end of a polypeptide up to the first 300 amino acids or ⅓ of the polypeptide, starting at the first amino acid of the polypeptide. The "amino terminal" region of a polypeptide is not shorter than 3 amino acids in length and not longer than 350 amino acids in length. Other possible lengths of the "amino terminal" region of a polypeptide include but are not limited to 5, 10, 20, 25, 50, 100 and 200 amino acids.

As used herein, the "carboxy terminal" region of a polypeptide refers to the polypeptide sequences encoded by polynucleotide sequences (double-stranded or single-stranded) located within or at the 3' end of a gene, and includes, but is not limited to, the 3' protein coding region of a gene. As used herein, the "carboxy terminal" region refers to the carboxy terminal end of a polypeptide up to 300 amino acids or ⅓ of the polypeptide from the last amino acid of the polypeptide. The "3' end" does not include the polyA tail, if one is present. The "carboxy terminal" region of a polypeptide is not shorter than 3 amino acids in length and not longer than 350 amino acids in length. Other possible lengths of the "carboxy terminal" region of a polypeptide include, but are not limited to, 5, 10, 20, 25, 50, 100 and 200 amino acids.

As used herein, the "internal polypeptide region" of a polypeptide refers to the polypeptide sequences located between the amino terminal region and the carboxy terminal region of a polypeptide, as defined herein. The "internal polypeptide region" of a polypeptide is not shorter than 3 amino acids in length and not longer than 350 amino acids in length. Other possible lengths of the "internal polypeptide region" of a polypeptide include, but are not limited to, 5, 10, 20, 25, 50, 100 and 200 amino acids.

The amino terminal, carboxy terminal and internal polypeptide regions of a polypeptide are non-overlapping and may, but need not be contiguous, and may, but need not, add up to the full length of the corresponding polypeptide.

As used herein, "polynucleotide" encompasses double-stranded DNA, single-stranded DNA and double-stranded or single-stranded RNA of more than 8 nucleotides in length.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oliognucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the probe sequence, the oligonucleotide primer typically contains 15-25 or more nucleotides, although it may contain fewer nucleotides. The factors involved in determining the appropriate length of primer are readily known to one of ordinary skill in the art.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length as long as it is less the full length of the target gene.

The oligonucleotides and analogs thereof may be RNA or DNA, or analogs of RNA or DNA, commonly referred to as antisense oligomers or antisense oligonucleotides. Such RNA or DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)—Oligonucleotide Analogues with an Achiral Peptide Backbone, (1992)).

Probes may also be mixtures of any of the oligonucleotide analog types together or in combination with native DNA or RNA. At the same time, the oligonucleotides and analogs thereof may be used alone or in combination with one or more additional oliognucleotides or analogs thereof.

As used herein, a "nucleic acid target" or a "nucleic acid marker" or a "nucleic acid member on an array" or "nucleic acid target on an array" also includes nucleic acid immobilized on an array and capable of binding to a nucleic acid member of complementary sequence through sets of non-covalent bonding interactions, including complementary base pairing interactions. As used herein, a nucleic acid target may include natural (i. e., A, G, C, or T) or modified bases (7-deazaguanosine, inosine, etc.). In addition, the bases in nucleic acid target may be joined by a linkage other than a phosphodiester bond, so long as it does not interfere with hybridization (i.e., the nucleic acid target still specifically binds to its complementary sequence under standard stringent or selective hybridization conditions). Thus, nucleic acid target may be peptide nucleic acids in which the constituent bases are joined by peptide bonds rather than phosphodiester linkages.

An "mRNA" means an RNA complimentary to a gene; an mRNA includes a protein coding region and also may include 5' end and 3' untranslated regions (UTR).

A "coding region" refers to a DNA encoding mRNA.

A "protein coding region" refers to the portion of the mRNA encoding a polypeptide.

As used herein, "mRNA integrity" refers to the quality of mRNA extracts from cartilage samples. mRNA extracts with good integrity do not appear to be degraded when examined by methods well known in the art, for example, by RNA agarose gel electrophoresis (e.g., Ausubel et al., John Weley & Sons, Inc., 1997, *Current Protocols in Molecular Biology*). Preferably, the mRNA samples have good integrity (e.g., less than 10%, preferably less than 5%, and more preferably less than 1% of the mRNA is degraded) to truly represent the gene expression levels of the cartilage samples from which they are extracted.

As used herein, "nucleic acid(s)" is interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As defined herein, a "nucleic acid array" refers a plurality of unique nucleic acids (or "nucleic acid members") attached to a support where each of the nucleic acid members is attached to a support in a unique pre-selected region. In one embodiment, the nucleic acid target attached to the surface of the support is DNA. In a preferred embodiment, the nucleic acid target attached to the surface of the support is either cDNA or oligonucleotides. In another preferred embodiment, the nucleic acid target attached to the surface of the support is cDNA synthesized by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein, the term "amplified", when applied to a nucleic acid sequence, refers to a process whereby one or more copies of a particular nucleic acid sequence is generated from a template nucleic acid, preferably by the method of polymerase chain reaction (Mullis and Faloona, 1987, Methods Enzymol., 155:335). "Polymerase chain reaction" or "PCR" refers to an in vitro method for amplifying a specific nucleic acid template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the probe nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a probe nucleic acid sequence contained within the template sequence, (ii) extending the primers wherein the nucleic acid polymerase synthesizes a primer extension product. "A set of polynucleotide primers" or "a set of PCR primers" can comprise two, three, four or more primers. In one embodiment, an exo-Pfu DNA polymerase is used to amplify a nucleic acid template in PCR reaction. Other methods of amplification include, but are not limited to, ligase chain reaction (LCR), polynucleotide-specific based amplification (NSBA), or any other method known in the art.

According to the invention, an array contemplates a specific set of genes immobilized to a solid support, or a set of corresponding 5' ends or a set of corresponding 3' ends or a set of corresponding internal coding regions. Of course, mixtures of a 5' end of one gene may be used as a target or a probe in combination with a 3' end of another gene to achieve the same result of OA diagnosis.

As used herein, "a plurality of" or "a set of" refers to more than two, for example, 3 or more, 100 or more, or 1000 or more, or 10,000 or more.

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

As used herein, "attaching" or "spotting" refers to a process of depositing a nucleic acid onto a solid substrate to form a nucleic acid array such that the nucleic acid is stably bound to the solid substrate via covalent bonds, hydrogen bonds or ionic interactions.

As used herein, "stably associated" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "solid substrate" or "solid support" refers to a material having a rigid or semi-rigid surface. The terms "substrate" and "support" are used interchangeably herein with the terms "solid substrate" and "solid support". The solid support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly) tetrafluoroethylene, (poly)vinylidendifluoride, polystyrene, polycarbonate, a charged membrane, such as nylon 66 or nitrocellulose, or combinations thereof. In a preferred embodiment, the solid support is glass. Preferably, at least one surface of the substrate will be substantially flat. Preferably, the solid support will contain reactive groups, including, but not limited to, carboxyl, amino, hydroxyl, thiol, and the like. In one embodiment, the solid support is optically transparent.

As used herein, "pre-selected region", "predefined region", or "unique position" refers to a localized area on a substrate which is, was, or is intended to be used for the deposit of a nucleic acid and is otherwise referred to herein in the alternative as a "selected region" or simply a "region." The pre-selected region may have any convenient shape, e.g., circular, rectangular, elliptical, wedge-shaped, etc. In some embodiments, a pre-selected region is smaller than about 1 cm$^2$, more preferably less than 1 mm$^2$, still more preferably less than 0.5 mm$^2$, and in some embodiments less than 0.1 mm$^2$. A nucleic acid member at a "pre-selected region", "predefined region", or "unique position" is one whose identity (e.g., sequence) can be determined by virtue of its position at the region or unique position.

As used herein "nucleic acid probe" or "nucleic acid probe marker" is defined as a nucleic acid capable of binding to a nucleic acid bound to an array of complementary sequence through sets of non-covalent bonding interactions including complementary base pairing interactions. The nucleic acid probe can either be an isolated nucleic acid sequence corresponding to a gene or portion thereof, or the nucleic acid probe can be total RNA or mRNA isolated from a sample. More preferably, the nucleic acid probes are single- or double-stranded DNA, RNA, or DNA-RNA hybrids, from human cartilage, total RNA extracts, and preferably from mRNA extracts.

In one embodiment, a conventional nucleic acid array of 'target' sequences bound to the array can be representative of the entire human genome, e.g. Affymetrix chip, and the isolated biomarker consisting of or comprising two or more of the genes described in FIGS. 1-7 or gene targets is applied to the conventional array.

In another embodiment, sequences bound to the array can be an isolated biomarker according to the invention and total cellular RNA is applied to the array.

As used herein, a "cartilage nucleic acid sample", refers to nucleic acids derived from cartilage. Preferably, a cartilage nucleic acid sample is total RNA, mRNA or is a nucleic acid corresponding to RNA, for example, cDNA. A cartilage nucleic acid sample can also include a PCR product derived from total RNA, mRNA or cDNA.

As used herein, the term "hybridizing to" or "hybridization" refers to the sequence specific non-covalent binding interactions with a complementary nucleic acid, for example interactions between a probe nucleic acid sequence and a target nucleic acid member on an array.

As used herein, "specifically hybridizes", "specific hybridization" or "selective hybridization" refers to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, *Nucleic acids Res.*, 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a target nucleic acid member on an array to a probe nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a probe nucleic acid will anneal to a target sequence. In particular, longer sequences have a higher melting temperature ($T_M$) than do shorter ones, and are less likely to be repeated within a given probe sequence, thereby minimizing promiscuous hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As used herein, the term "differential hybridization" refers to a difference in the quantitative level of hybridization of a nucleic acid target to a first complementary nucleic acid probe as compared with the hybridization of the same nucleic acid target to a control nucleic acid probe. "Differential hybridization" can also refer to a difference in the quantitative level of hybridization of a first nucleic acid target to a nucleic acid probe as compared with a second control nucleic acid target. A "differential hybridization" means that the ratio of the level of hybridization of the first sample as compared with the control is not equal to 1.0. For example, the ratio of the level of hybridization of the target to the first probe as compared to the second probe is greater than or less than 1.0, and includes greater than 1.5 and less than 0.7, greater than 2 and less than 0.5. A differential hybridization also exists if the hybridization is detectable in one sample but not another sample.

As used herein, the term "differential expression" refers to a difference in the level of expression of a gene, as measured by the amount or level of RNA, including mRNA, complementary to the gene, in one sample as compared with the level of expression of the same gene in a second sample. Differential expression can be determined as a result of differential hybridization or through other known methods in the art used to measure the level or amount of mRNA expression.

As used herein the term "differential expression" also refers to a difference in the level of expression of a gene, as measured by the amount or level of protein encoded by the gene, in one sample as compared with the amount or level of protein expression of the same gene in a second sample. Differential protein expression can be determined as a result of binding to monoclonal antibodies that are specific for the particular protein or through other known methods in the art used to measure the level or amount of protein expression.

"Differentially increased expression" refers to 1.1 fold, 1.2 fold, 1.4 fold, 1.6 fold, 1.8 fold or more. "Differentially decreased expression" refers to less than 1.0 fold, 0.8 fold, 0.6 fold, 0.4 fold, 0.2 fold, 0.1 fold or less.

As used herein, the term "control" or "control sample" in the context of this invention refers to one or more cartilage nucleic acid samples isolated from an individual or group of individuals who are classified as normal. A control or control sample can also refer to a sample isolated from a group of patients diagnosed with disease including patients diagnosed with OA, or a patients diagnosed with a specific stage of OA. The term control or control sample can also refer to the compilation of data derived from samples of one or more individuals classified as normal or one or more individuals diagnosed with disease or a stage of disease, or one or more individuals having undergone treatment of disease.

As used herein, the term "up regulated" or "increased level of expression" in the context of this invention refers to a sequence corresponding to a gene which is expressed wherein the measure of the quantity of the sequence demonstrates an increased level of expression of the gene, as can be determined using array analysis or other similar analysis, in cartilage isolated from an individual having osteoarthritis or an identified disease state of osteoarthritis as determined by osteoarthritis staging as compared with the same gene in cartilage isolated from normal individuals or from an individual with a different identified disease state of osteoarthritis as determined by osteoarthritis staging. An "increased level of expression" according to the present invention, is an increase in expression of at least 10% or more, for example, 20%, 30%, 40%, or 50%, 60%, 70%, 80%, 90% or more, or greater than 1-fold, 2-fold, 3-fold, 4-fold, 5-fold, 10-fold, 50-fold, 100-fold or more as measured, for example, by the intensity of hybridization according to methods of the present invention. For example, up regulated sequences includes sequences having an increased level of expression in cartilage isolated from individuals characterized as having mild, moderate, marked or severe OA as compared with cartilage isolated from normal individuals.

As used herein, the term "down regulated" or "decreased level of expression" in the context of this invention refers to a sequence corresponding to a gene which is expressed wherein the measure of the quantity of the sequence demonstrates a decreased level of expression of the gene, as can be determined using microarray analysis or other similar analysis, in cartilage isolated from an individual having osteoarthritis or an identified disease state of osteoarthritis as determined by osteoarthritis staging as compared with the same gene in cartilage isolated from normal individuals or from an individual having a different identified disease state of osteoarthritis as determined by osteoarthritis staging. A "decreased level of expression" according to the present invention, is a decrease in expression of at least 10% or more, for example, 20%, 30%, 40%, or 50%, 60%, 70%, 80%, 90% or more, or a decrease of greater than 1-fold, 2-fold, 3-fold, 4-fold, 5-fold, 10-fold, 50-fold, 100-fold or more as measured, for example, by the intensity of hybridization according to methods of the present invention. For example, down regulated sequences includes sequences having a decreased level of expression in cartilage isolated from individuals characterized as having mild, moderate, marked or severe OA as compared with cartilage isolated from normal individuals.

As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.).

The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: $Tm=81.5+16.6(\log[Na+])+0.41(\text{fraction G+C})-(600/N)$ where N is the length of the oligonucleotide.

For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature may be calculated using the equation $Tm=81.5+16.6(\log[Na^+])+0.41(\text{fraction G+C})-(0.63\% \text{formamide})-(600/N)$, where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "level of expression" refers to the measurable quantity of a given nucleic acid as determined by hybridization (relative to a control) or more quantitative measurements such as real-time RT PCR, which includes use of both SYBR® green and TaqMan® technology and which corresponds in direct proportion with the extent to which the gene is expressed. The level of expression of a nucleic acid is determined by methods well known in the art. The term "differentially expressed" or "difference in the level of expression" refers to an increase or decrease in the measurable expression level of a given nucleic acid as compared with a control. As used herein, "differentially expressed" or "change in the level of expression" when referring to microarray analysis, or real-time RT PCR means the ratio of the level of expression of a given polynucleotide in one sample and the expression level of the given polynucleotide in another sample is not equal to 1.0. "Differentially expressed" or "change in the level of expression" when referring to microarray analysis or real-time RT PCR according to the invention also means the ratio of the expression level of a given polynucleotide in one sample and the expression level of the given polynucleotide in another sample where the ratio is greater than or less than 1.0 and includes greater than 1.5 and less than 0.7, as well as greater than 2.0 and less than 0.5. A nucleic acid also is said to be differentially expressed in two samples if one of the two samples contains no detectable expression of the nucleic acid. Absolute quantification of the level of expression of a nucleic acid can be accomplished by including known concentration(s) of one or more control nucleic acid species, generating a standard curve based on the amount of the control nucleic acid and extrapolating the expression level of the "unknown" nucleic acid species from the real-time RT PCR hybridization intensities of the unknown with respect to the standard curve.

As used herein, the "level of expession of a biomarker" refers to the measurable quantity of each gene of the biomarker as determined by hybridization relative to an internal standard.

As used herein, a "difference of the level of expression" when referring to a biomarker indicates a change in the ratio of the level of expression of each gene of the biomarker as compared to a biomarker control wherein the biomarker control is comprised of two populations: a) a population that has been confirmed as not having OA (normal population) using those means known in the art, and b) a control population of individuals having OA or having a specific stage of OA (disease population), wherein the disease population has been confirmed to have OA or a specific stage of OA using those means known in the art, wherein the changes in the ratio of the level of expression of each gene of the biomarker when properly weighted and compared to a normal population and a disease population is such that using a ROC analysis (Basic Principles of ROC Analysis Metz. E. Nuclear Medicine 8, 4 (1978)) or a similar statistical method (MedCalc Software for Windows, Medcalc™ version 7.2, Belgium) a person of skill in the art can determine that a patient is correctly classified as having OA or having a specific stage of OA.

For microarray analysis, the level of expression is measured by hybridization analysis using labeled probe nucleic acids according to methods well known in the art. The label on the probe nucleic acid can be a luminescent label, an enzymatic label, a radioactive label, a chemical label or a physical label. Preferably, probe nucleic acids are labeled with a fluorescent molecule. Preferred fluorescent labels include, but are not limited to: fluorescein, amino coumarin acetic acid, tetramethylrhodamine isothiocyanate (TRITC), TEXAS RED, Cyanine 3 (CY3) and Cyanine 5 (CY5).

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, *Nucl. Acids Res.*, 25:3389-3402; Schäffer, A. A. et al., 1999, *Bioinformatics* 15:1000-1011). As used herein, "significant match" encompasses non-contiguous or scattered identical nucleotides so long as the sequences exhibit at least 65%, and preferably, at least 70%, at least 75%, at least 80%, at least 85%, and preferably, at least 90% identity, when maximally aligned using alignment methods routine in the art.

As used herein, a "gene expression pattern" or "gene expression profile" or "nucleic acid array expression profile" comprises the pattern of differential hybridization of a plurality of probe nucleic acid sequences hybridized to a plurality of nucleic acid targets on an array as compared with a control.

As used herein, "indicative of disease" refers to an expression pattern which is diagnostic of disease or a stage of disease such that the expression pattern is found significantly more often in patients with a disease or a stage of disease than in patients without the disease or another stage of disease (as determined using routine statistical methods setting confidence levels at a minimum of 95%). Preferably, an expression pattern which is indicative of disease is found in at least 60% of patients who have the disease and is found in less than 10% of patients who do not have the disease. More preferably, an expression pattern which is indicative of disease is found in at least 70%, at least 75%, at least 80%, at least 85%, at least 90%, at least 95% or more in patients who have the disease and is found in less than 10%, less than 8%, less than 5%, less than 2.5%, or less than 1% of patients who do not have the disease.

As used herein, a "therapeutic agent" or "agent" refers to a compound that increases or decreases the expression of one or more polynucleotide sequence that is differentially expressed in a chondrocyte from any two of the following developmental or osteoarthritis disease stages: (a) mild, (b) moderate, (c) marked and (d) severe, or (e) chondrocyte from a normal individual, as defined herein. A therapeutic agent according to the invention also refers to a compound that increases or decreases the anabolic activity of a chondrocyte. The invention provides for a "therapeutic agent" that 1) prevents the onset of osteoarthritis; 2) reduces, delays, or eliminates osteoarthritis symptoms such as pain, swelling, weakness and loss of functional ability in the afflicted joints; 3) reduces, delays, or eliminates cartilage degeneration, and/or enhances chondrocyte metabolic activity and cell division rates; and/or 4) restores one or more expression profiles of one or more disease-indicative nucleic acids of a patient to a profile more similar to that of an individual having an earlier stage of disease or normal individual when administered to a patient.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the reduction of the symptoms of osteoarthritis or the prevention of osteoarthritis progression as described in the present specification. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

As used herein, a "ligand" is a molecule that specifically binds to a polypeptide encoded by one of the genes of a biomarker of the invention. A ligand can be a nucleic acid (RNA or DNA), polypeptide, peptide or chemical compound.

A ligand of the invention can be a peptide ligand, e.g., a scaffold peptide, a linear peptide, or a cyclic peptide. In a preferred embodiment, the polypeptide ligand is an antibody. The antibody can be a human antibody, a chimeric antibody, a recombinant antibody, a humanized antibody, a monoclonal antibody, or a polyclonal antibody. The antibody can be an intact immunoglobulin, e.g., an IgA, IgG, IgE, IgD, IgM or subtypes thereof. The antibody can be conjugated to a functional moiety (e.g., a compound which has a biological or chemical function (which may be a second different polypeptide, a therapeutic drug, a cytotoxic agent, a detectable moiety, or a solid support. A polypeptide ligand e.g. antibody of the invention interacts with a polypeptide, encoded by one of the genes of a biomarker, with high affinity and specificity. For example, the polypeptide ligand binds to a polypeptide, encoded by one of the genes of a biomarker, with an affinity constant of at least $10^7 \, M^{-1}$, preferably, at least $10^8 \, M^{-1}$, $10^9 \, M^{-1}$, or $10^{10} \, M^{-1}$.

As used herein, the term "specifically binds" refers to the interaction of two molecules, e.g., a ligand and a protein or peptide, wherein the interaction is dependent upon the presence of particular structures on the respective molecules. For example, when the two molecules are protein molecules, a structure on the first molecule recognizes and binds to a structure on the second molecule, rather than to proteins in general. "Specific binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antibody" also encompasses antigen-binding fragments of an antibody. The term "antigen-binding fragment" of an antibody (or simply "antibody portion," or "fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

Identifying Chondrocyte Enriched and Chondrocyte-Specific Polynucleotide Sequences cDNA libraries were constructed from human fetal, normal, mild, moderate, marked and/or severe osteoarthritic cartilage samples. The known and novel clones derived from these libraries were then used to construct human chondrocyte-specific microarrays to generate differential gene expression profiles useful as a diagnostic tool for detection of mild (early stage) osteoarthritis. Arrays of the invention are useful as a gold standard for osteoarthritis diagnosis and for use to identify and monitor therapeutic efficacy of new drug targets.

One effective and rapid way of characterizing gene expression patterns in a given tissue is through large-scale partial sequencing of a cDNA library produced from such a tissue to generate expressed sequence tags (ESTs). This approach has provided both quantitative and qualitative information on gene expression in a variety of tissues and cells (Adams M D, Kerlavage A R, Fleischmann R D, Fuldner R A, Bult C J, Lee N H, et al. Initial assessment of human gene diversity and expression patterns based upon 83 million nucleotides of cDNA sequence. Nature 1995;377 Suppl:3-174.); (Hwang D M, Dempsey A A, Wang R X, Rezvani M, Barrans J D, Dai K S, et al. A Genome-Based Resource for Molecular Cardiovascular Medicine: Toward a Compendium of Cardiovascular Genes. Circulation 1997;96:4146-203.); (Mao M, Fu G, Wu J S, Zhang Q H, Zhou J, Kan L X, et al. Identification of genes expressed in human CD34+ hematopoietic stem/progenitor cells by expressed sequence tags and efficient full-length cDNA cloning. Proc Natl Acad Sci 1998;95:8175-80);

(Hillier L D, Lennon G, Becker M, Bonaldo M F, Chiapelli B, Chissoe S, et al. Generation and analysis of 280,000 human expressed sequence tags. Genome Res. 1996;6:807-28). Since cDNA libraries represent gene transcription in the cells of the tissue used to construct the library, gene expression profiles generated by random sampling and sequencing is used for detailed genetic-level comparison between developmental, normal and pathological states of the tissue examined.

Many human genes are expressed at different levels in cartilage of different disease states. In some cases, a gene is not expressed at all in some disease states, and at high levels in others. According to the invention, differential analysis of chondrocyte gene expression during different stages of cartilage developmental and in different disease states using an EST-based approach has identified genes that play important roles in osteoarthritis pathogenesis and cartilage repair. The advantage of this method is that it provides gene expression information on a larger scale than other methods. The cDNA clones generated by this approach are also useful for functional studies of certain genes. This type of genomic-based approach has provided important novel insights into our understanding of the osteoarthritis disease process and provides for novel diagnostic, prognostic and therapeutic approaches.

Identification of Biomarkers Useful in Diagnosis of OA

The invention provides stage-specific genes identifiable in a sample (Tables 1-7) whose level of expression is indicative of the existence of some degree of mild, moderate, marked or severe osteoarthritis when compared with the level of expression of the same one or more genes in a normal individual. These genes, or the products of these genes, in combination are therefore useful as biomarkers to identify individuals having OA.

It would be understood by a person skilled in the art that two or more of these genes, or the products of these genes in combination are useful as biomarkers.

More specifically the number of useful combinations is described (Feller, W. F. , Intro to Probability Theory, $3^{rd}$ Ed. Volume 1, 1968, ed. J. Wiley) and can be calculated using the general formula:

$$x!/(n)! (x-n)!$$

where n is the number of genes to be selected for the combination and x is the number of genes to be considered.

For example there are $$\frac{21!}{2!(21-2)!} = \frac{5.1 \ 10^{19}}{2.432 \ 10^{17}} = 210$$

possible combinations of two genes amongst the 21 genes that are down regulated in severe OA (Table 2).

Similarly there are 21!/3!(21−3)! Possible combinations of three genes amongst the 21 genes that are down regulated in severe OA (Table 2).

Identification of Biomarkers Useful in Identification of Stage Specific OA

The invention further provides genes as set forth in Tables 1-7 whose level of expression is distinctive for at least one stage of osteoarthritis as compared with another stage of osteoarthritis. For example, the invention provides for genes which have been identified as being down regulated (Table 1) or up-regulated (Table 3) in cartilage isolated from patients having mild osteoarthritis, but which are not neither down-regulated (Table 1) or up-regulated (Table 3) in patients having severe osteoarthritis, when compared with cartilage isolated from normal individuals. Similarly, the invention provides for genes which have been identified as being down regulated (Table 2) or up-regulated (Table 4) in cartilage isolated from patients having severe osteoarthritis, but which are not down regulated (Table 2) or up-regulated (Table 4) in patients having mild osteoarthritis, when compared with cartilage isolated from normal individuals. The invention also provides for genes that are differentially expressed at specific stages of OA e.g. mild OA only (Tables 6a and 7a), moderate OA only (Table 6b), marked OA only (Table 6c) or severe OA only (Tables 6d and 7b). The invention further provides for genes that are up-regulated in severe OA and down regulated in mild OA (Table 5).

These genes, portions of these genes, or products of these genes, either singly or in combination, are therefore useful as biomarkers to identify the stage of OA of a patient. These genes, portions thereof, or the products of these genes, either singly or in combination, are also useful as biomarkers to identify the efficacy of treatment (e.g. to be able to identify regression of disease stage as a result of successful treatment).

Methods of Using Biomarkers of the Invention to Diagnose OA

The invention contemplates the use of the genes set out in Tables 1-7 as biomarkers of OA whose level of expression is indicative of the existence of osteoarthritis when compared with the level of expression of the same gene in a normal individual. The level of expression of the biomarkers of the invention can be determined by measuring the level of the protein products of the genes, or may be determined by measuring the expression of mRNA utilizing oligonucleotides, ESTs, cDNA, DNA or RNA, or portions thereof, corresponding to one or more genes of the invention to measure the level of expression.

Oligonucleotides, ESTs, cDNA, DNA or RNA or portions thereof, for example, can be used as nucleic acid targets immobilized on an array and hybridized to total RNA, mRNA, cDNA or RT-PCR specific to one or more genes of the invention, or portions thereof, to measure the level of expression of mRNA corresponding to these genes of a test individual as compared with a control wherein differential hybridization as between the sample of the test individual as compared with the control is indicative of OA.

The invention further contemplates the use of total RNA, mRNA, cDNA or RT-PCR products corresponding to one or more genes of the invention, or portions thereof, wherein said nucleic acids can be utilized as nucleic acid probes hybridized with a commercial array (such as Affymetrix Affy U133) or a manufactured array, wherein the array is comprised of oligonucleotides cDNAs, ESTs, or DNA corresponding to one or more of the genes of the human genome. The level of hybridization of the RT-PCR products to the array as compared with a control is measured and differential hybridization of said RT-PCR products as compared with the control is indicative of OA.

The invention further contemplates the use of techniques such as quantitative real-time RT PCR (for example using SYBR®Green or TaqMan® labelled probes complementary to a gene of the invention) to determine levels of mRNA expression of the genes of the invention as compared with a control as a means of diagnosing OA.

The invention further contemplates the use of techniques known to persons skilled in the art (for example, techniques such as Western Blotting, Immunoprecipitation protein microarray analysis and the like) to measure the level of proteins corresponding to the genes of the invention to determine levels of expression of the genes of the invention as compared with a control as a means of diagnosing OA.

Thus, in one embodiment, the method of determining whether a person has OA comprises the steps of (a) hybridizing nucleic acid probes corresponding to RNA, mRNA, cDNA or RT-PCR products from a test individual to an array having one or more oligonucleotides, ESTs, cDNAs, DNA or RNA, or portions thereof corresponding to one or more genes of the invention spotted onto the array; (b) measuring the amount of hybridization of each sample to each unique location on the array; and (c) comparing the amount of hybridization of the nucleic acid probes of the test individual to the array as compared with a control wherein differential hybridization of the test sample as compared with the control is indicative of the test individual having OA.

In another embodiment, the method of determining whether a person has OA comprises the steps of (a) isolating total cellular protein from a test individual; (b) generating monoclonal antibodies specific for the polypeptides encoded by one or more genes, or portions thereof, of the invention for use as an antibody target (c) spotting the antibody targets of step (b) to an array; and (d) incubating the total cellular protein from a test individual to said array; and (e) measuring the amount of binding at each unique location on the array; and (f) comparing the amount of binding of the total cellular protein of the test individual to a control wherein the control uses total cellular protein derived from a normal individual.

Methods of Using Biomarkers of the Invention to Determine Progression of OA

The invention contemplates the use of genes as set out in Tables 1-7, or combinations thereof, whose level of expression is indicative of the existence of a certain stage of osteoarthritis. The expression levels of the marker genes in a sample may be determined by any means known in the art. For example, the level of expression of the biomarkers of the invention can be determined by measuring the level of the protein products of the genes, or may be determined utilizing oligonucleotides, ESTs, cDNA, DNA or RNA, or portions thereof, corresponding to one or more genes of the invention to measure the level of expression.

In one embodiment of the invention, oligonucleotides, ESTs, cDNA, DNA or RNA, or portions thereof, corresponding to one or more genes of the invention, are used as nucleic acid targets on an array to measure the level of expression of mRNA corresponding to these genes of a test individual as compared with a control wherein differential expression of said mRNA as compared with the control is useful as a means of determining the progression or regression of OA of the test individual.

The invention further contemplates the use of total RNA, mRNA, cDNA or RT-PCR products corresponding to one or more genes of the invention, or portions thereof, wherein said nucleic acids can be utilized as nucleic acid targets hybridized with a commercial array (such as Affymetrix Affy U133) or a manufactured array wherein the array is comprised of oligonucleotides, cDNAs or ESTs corresponding to one or more of the genes of the human genome wherein the level of hybridization of the RT-PCR products as compared with a control is useful as a means of determining the progression or regression of OA of the test individual.

The invention further contemplates the use of techniques such as quantitative real-time RT PCR (for example using SYBR®Green or TaqMan® labelled probes complementary to a gene of the invention) to determine levels of mRNA expression corresponding to the genes of the invention as compared with a control as a means of determining the progression or regression of OA of the test individual.

The invention further contemplates the use of techniques known to persons skilled in the art (for example, techniques such as Western Blotting, Immunoprecipitation, Protein arrays and the like) to measure the level of proteins corresponding to the gene of the invention to determine levels of expression of the genes of the invention as compared with a control as a means of determining progression or regression of OA of the test individual.

Thus, in one embodiment, the method of determining whether a person has OA comprises the steps of (a) hybridizing nucleic acid probes corresponding to RNA, mRNA or cDNA or RT-PCR products from a test individual to an array having one or more oligonucleotides, ESTs, cDNAs, DNA, RNA, or portions thereof corresponding to a gene of the invention spotted onto the array; (b) measuring the amount of hybridization of each unique location on the array; and (c) comparing the amount of hybridization of the nucleic acid probes of the test individual to a control wherein the control uses nucleic acid probes derived from a normal individual or derived from an individual having a different stage of OA as a means of determining disease progression or regression.

Thus, in another embodiment, the method of determining whether a person has OA comprises the steps of (a) incubating total protein from a sample of a test individual to a protein array having one or more monoclonal antibodies that specifically bind to a polypeptide encoded by a gene of the invention spotted onto the array; (b) measuring the amount of binding at each unique location on the array; and (c) comparing the amount of binding of the total cellular protein of the test individual to a control wherein the control uses total cellular protein derived from a normal individual or derived from an individual having a different stage of OA as a means of determining disease progression or regression.

Samples

Cartilage

In one aspect, cartilage is obtained from a fetus using methods known in the art. The chondrocytes of fetal cartilage have a higher level of metabolic activity and cell division rates as compared to chondrocytes from cartilage from either a normal adult or from an individual diagnosed with any stage of osteoarthritis (mild, moderate, marked and severe).

In another aspect, cartilage is obtained from a normal individual who is alive or is obtained from cartilage tissue less than 14 hours post mortem, according to methods known in the art and described below. Normal articular cartilage from human adults are obtained using any known method. However, truly normal cartilage cannot generally be sampled from live donors due to ethical considerations. Preferably, normal cartilage samples are obtained from deceased donors, within a fourteen-hour post-mortem window after cessation of perfusion to the sampled joint, to minimize the degradation of RNA observed beyond the window. In other embodiments, the "normal" tissue is obtained less than 14 hours post-mortem, such as 13, 12, 11, 10, 9, 8, 6, 4, 2, or 1 hour post-mortem. A baboon study was conducted to confirm this approach and is described herein below in Example 11. Preferably the normal cartilage is obtained less than 14 hours post-mortem. More prefably, the normal cartilage is obtained less than 12 hours post-mortem.

In another aspect of the invention, cartilage also is isolated from the following disease stages of osteoarthritis: mild, marked, moderate and severe. Human cartilage samples from osteoarthritic individuals are obtained using any known method. Preferably the cartilage is obtained from individuals undergoing arthroscopy or total knee replacements and samples are stored in liquid nitrogen until needed. In a preferred embodiment, a minimum of 0.05 g of cartilage sample is isolated to obtain 2 µg total RNA extract for the construction of a cDNA library. In another preferred embodiment, a minimum of 0.025 g cartilage sample is isolated to obtain 1 µg total RNA extract to use as a probe sample for a microarray. A cartilage sample that is useful according to the invention is in an amount that is sufficient for the detection of one or more nucleic acid sequences according to the invention.

Developmental and Disease Stages of Articular Cartilage

Chondrocytes were preferably obtained from any of the following developmental and disease stages: fetal, normal, mild osteoarthritic, moderate osteoarthritic, marked osteoarthritic or severe osteoarthritic.

Cartilage isolated from a human fetus (e.g., during fetal development) is characterized above, and is useful according to the invention for analysis of fetal chondrocytes.

Cartilage isolated from a "normal" individual, defined herein, also is useful according to the invention for isolation and analysis of "normal" chondrocytes.

Cartilage isolated from a patient diagnosed with any one of: mild, moderate, marked and severe osteoarthritis also is useful in the present invention.

In order to classify cartilage according to disease state, a scoring system is used, whereby subjective decisions by the arthroscopist are minimized. The scoring system which defines disease states described herein is that of Marshall, supra, incorporated herein by reference. According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A scoring system is then applied in which each articular surface receives an osteoarthritis severity number value that reflects the cartilage severity grade for that surface, as described in Table 8.

TABLE 8

Articular Cartilage Grading System

| Grade | Articular Cartilage | Points |
|-------|---------------------|--------|
| 0 | Normal | 0 |
| I | Surface intact-softening, edema | 1 |
| II | Surface-disrupted-partial thickness lesions (no extension to bone) | 2 |
| III | Full thickness lesions-extensions to intact bone | 3 |
| IV | Bone erosion or eburnation | 4 |

For example, if the medial femoral condyle has a grade I lesion as its most severe cartilage damage, a value of 1 is assigned. A total score for the patient is then derived from the sum of the scores of the 6 articular surfaces. Based on the total score, each patient is placed into one of 4 osteoarthritis groups: mild (1-6), moderate (7-12), marked (13-18) and severe (>18).

RNA Preparation

In one aspect, RNA is isolated from cartilage samples from various disease or developmental stages as described herein. Samples can be from single patients or can be pooled from multiple patients.

Total RNA is extracted from the cartilage samples according to methods well known in the art. In one embodiment, RNA is purified from cartilage tissue according to the following method. Following removal of a tissue of interest from an individual or patient, the tissue is quick frozen in liquid nitrogen, to prevent degradation of RNA. Upon the addition of a volume of tissue guanidinium solution, tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-Cl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18:5294).

Alternatively, RNA is isolated from cartilage tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 µl DEPC-treated water or DEPC-treated 0.5% SDS (Chomczynski and Sacchi, 1987, *Anal. Biochem.*, 162: 156).

Preferably, the cartilage samples are finely powdered under liquid nitrogen and total RNA is extracted using TRIzol® reagent (GIBCO/BRL). Purity and integrity of RNA is assessed by absorbance at 260/280 nm and agarose gel electrophoresis followed by inspection under ultraviolet light.

Construction of cDNA Libraries cDNA libraries are constructed according to methods well known in the art (see for example Ausubel, supra, and Sambrook, supra, incorporated herein by reference).

In one aspect, cDNA samples, i.e., DNA that is complementary to RNA such as mRNA are prepared. The preparation of cDNA is well-known and well-documented in the prior art.

cDNA may be prepared according to the following method. Total cellular RNA is isolated (as described) and passed through a column of oligo(dT)-cellulose to isolate polyA RNA. The bound polyA mRNAs are eluted from the column with a low ionic strength buffer. To produce cDNA molecules, short deoxythymidine oligonucleotides (12-20 nucleotides) are hybridized to the polyA tails to be used as primers for reverse transcriptase, an enzyme that uses RNA as a template for DNA synthesis. Alternatively, or additionally, mRNA species are primed from many positions by using short oligonucleotide fragments comprising numerous sequences complementary to the mRNA of interest as primers for cDNA synthesis. The resultant RNA-DNA hybrid is converted to a double stranded DNA molecule by a variety of enzymatic steps well-known in the art (Watson et al., 1992, *Recombinant DNA*, 2nd edition, Scientific American Books, New York).

To construct a cDNA library, the poly(A)+ RNA fraction may be isolated by oligo-dT cellulose chromatography (Pharmacia), and 3-5 ug poly(A)+ RNA is used to construct a cDNA library in the λ ZAP Express vector (Stratagene). Alternatively, cDNA libraries may be constructed into λTriplEx2 vector through a PCR-based method, using SMART (Switching Mechanism At 5' end of RNA Transcript) cDNA Library Construction Kit (Clontech). First-strand cDNA is synthesized with an Xho I-oligo (dT) adapter-primer in the presence of 5'-methyl dCTP. After second-strand synthesis and ligation of EcoRI adapters, the cDNAs are digested with Xho I, resulting in cDNA flanked by EcoRI sites at the 5'-ends and Xho I sites at the 3'-ends. Digested cDNAs are size-fractionated in Sephacryl S-500 spin columns (Stratagene), then ligated into the λ ZAP Express vector predigested with EcoRI and Xho I. The resulting DNA/cDNA concatomers are packaged using Gigapack Gold packaging extracts. After titration, aliquots of primary packaging mix are stored in 7% DMSO at −80° C. as primary library stocks, and the rest are amplified to establish stable library stocks.

From the amplified library, phage plaques are plated onto an appropriate medium. Preferably, phage plaques are plated at a density of 200-500 pfu/150 mm plate onto an *Escherichia coli* XL1-blue MRF' lawn with IPTG/X-gal for color selection. The plaques are then randomly picked and positive inserts are identified by polymerase chain reaction (PCR), according to methods well known in the art and described hereinbelow. Preferably, plaques are picked into 75 ul suspension media buffer (100 mM NaCl, 10 mM $MgSO_4$, 1 mM Tris, pH7.5, 0.02% gelatin). Phage elutes (5 ul) may be used for PCR reactions (50 ul total volume) with 125 umol/L of each dNTP (Pharmacia), 10 pmol each of modified T3 (5'-GCCAAGCTCGAAATTAACCCTCACTAAAGGG-3' (SEQ ID NO: 19)) and T7 (5'-CCAGTGAATTGTAATAC-GACTCACTATAGGGCG-3' (SEQ ID NO: 20)) primers, and 2 U of Taq DNA polymerase (Pharmacia). Reactions are cycled in a DNA Thermal Cycler (Perkin-Elmer) [denaturation at 95° C. for 5 minutes, followed by 30 cycles of amplification (94° C., 45 seconds; 55° C., 30 seconds; 72° C., 3 minutes) and a terminal isothermal extension (72° C., 3 minutes)]. Agarose gel electrophoresis is used to assess the presence and purity of inserts.

The PCR product is then subjected to DNA sequencing using known methods (see Ausubel et al., supra and Sambrook et al., supra). Methods of sequencing employ such enzymes as the Klenow fragment of DNA polymerase I, Sequenase® (US Biochemical Corp, Cleveland, Ohio), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System (Gibco BRL, Gaithersburg, Md.). Preferably, the process is automated with machines such as the Hamilton Micro Lab 2200 (Hamilton, Reno Nev.), Peltier Thermal Cycler (PTC200; MJ Research, Watertown, Mass.), the ABI 377 DNA sequencers (Perkin Elmer), and the PE Biosystems ABI Prism 3700 DNA Analyzer.

PCR products are first subjected to DNA sequencing reactions using specific primers, BigDye™ Terminator Cycle Sequencing v2.0 Ready Reaction (PE Biosystems), Tris MgCl buffer and water in a thermocycler. Sequencing reactions were incubated at 94° C. for 2 minutes, followed by 25 cycles of 94° C., 30 seconds; 55° C., 20 seconds; and 72° C., 1 minute; and 15 cycles of 94° C., 30 seconds; and 72° C. for 1 minute; and 72° C. for 5 minutes Reactions were then put on hold at 4° C. until purified using methods well known in the prior art (i.e. alcohol precipitation or ethanol precipitation). Automated sequencing is preferably carried out with a PE Biosystems ABI Prism 3700 DNA Analyzer.

PCR

In one aspect, nucleic acid sequences of the invention are amplified by the polymerase chain reaction (PCR). PCR methods are well-known to those skilled in the art.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, *Methods Enzymol.*, 155: 335, herein incorporated by reference.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10H PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Several techniques for detecting PCR products quantitatively without electrophoresis may be useful according to the invention. One of these techniques, for which there are commercially available kits such as Taqman™ (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The Taqman™ system has the additional advantage of not requiring gel electrophoresis and allows for quantification when used with a standard curve.

Nucleic Acid Sequences Useful According to the Invention

The invention provides for isolated nucleic acid sequences including ESTs which can be used as targets, arrayed on microarrays, and/or used for the development of therapies to treat osteoarthritis.

In one aspect, the invention is to monitor cartilage gene expression profiles of osteoarthritis patients diagnosed with different stages of osteoarthritis. A second aspect of the invention is to screen for potential therapeutic agents which alter the gene expression profile of diseased cartilage cells. The invention therefore provides for nucleic acid sequences that are present at each of the following disease stages: normal, mild osteoarthritic, moderate osteoarthritic, marked osteoarthritic and severe osteoarthritic. The invention also provides for nucleic acid sequences that are differentially expressed in any two of the following developmental and disease stages: normal, fetal, mild osteoarthritic, moderate osteoarthritic, marked osteoarthritic and severe osteoarthritic.

Nucleic acids useful according to the invention are prepared by isolating cartilage tissue samples from a developmental or disease stage (normal, fetal, mild osteoarthritic, moderate osteoarthritic, marked osteoarthritic and severe osteoarthritic), preparing a cDNA library (as described above), and performing large-scale partial sequencing (described herein) of the cDNA library to generate Expressed Sequence Tags (ESTs). An EST useful according to the invention is preferably in the range of 50-1000 nucleotides and most preferably 50-500 nucleotides in length.

The invention provides for nucleic acid sequences or ESTs that are categorized as "novel" or "known", including "known sequences with a function" and "known sequences without a known function", all defined herein.

Nucleic Acid Members and Targets

In one aspect, the invention provides nucleic acid members and targets that bind specifically to a probe nucleic acid sequence (e.g., present in a cartilage nucleic acid sample).

Nucleic acid members are stably associated with a solid support to comprise an array according to the invention. The length of a nucleic acid member can range from 50 to 6000 nucleotides, 100 to 500 nucleotides, and in other embodiments, from 500 to 1500 nucleotides. The nucleic acid members may be single or double stranded, and/or may be PCR fragments amplified from cDNA.

The invention also provides for nucleic acid sequences comprising a probe. In a certain embodiment, a probe is labeled, according to methods known in the art. A probe according to the invention is 50 to 5000 nucleotides, more preferably 100-500 nucleotides and most preferably 50 to 250 nucleotides in length. The probe may be single or double stranded, and may be a PCR fragment amplified from cDNA.

The nucleic acid members and targets according to the invention can be used to detect probe sequences such as chondrocyte enriched or chondrocyte-specific sequences, and preferably sequences whose presence in a sample are indicative, or diagnostic or prognostic, of a stage of osteoarthritis.

The probe nucleic acid sequences to be analyzed are preferably from human cartilage and preferably comprise RNA or nucleic acid corresponding to RNA, (i.e., cDNA or amplified products of RNA or cDNAs).

Polypeptides and Antibodies

In one aspect, the invention provides for antibodies that are bound to an array and selectively bind to the polypeptides encoded by two or more of the genes of an isolated biomarker (e.g., labelled proteins encoded by the nucleotide sequences of Tables 1-7). The invention also provides for the production and purification of the polypeptides encoded by the genes of an isolated biomarker as well as the isolation, characterization and production of monoclonal antibodies that bind to the polypeptides encoded by the genes described in Tables 1-7.

Protein Production

Standard recombinant nucleic acid methods can be used to express a polypeptide or antibody of the invention. Generally, a nucleic acid sequence encoding the polypeptide is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Polypeptides comprising the 5' region, 3' region or internal coding region of a gene of an isolated biomarker as defined herein, are expressed from nucleic acid expression vectors containing only those nucleotide sequences corresponding to the 5' region, 3' region or internal coding region of a gene of an isolated biomarker. Methods for producing antibodies directed to full length polypeptides encoded by the genes described in Tables 1-7 or polypeptides encoded by the 5' region, 3' region or internal coding regions of the genes described in Tables 1-7 are provided below.

The expression vector for expressing the polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, PBLUE-SCRIPT SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli*, *Bacillus subtilis*, *Salmonella typhimurium* and various species within the genera *Pseudomonas*, *Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention further provides host cells containing the vectors of the present invention, wherein the nucleic acid has been introduced into the host cell using known transformation, transfection or infection methods. For example, the host cells can include members of a library constructed from the diversity strand. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)).

Any host/vector system can be used to identify one or more of the target elements of the present invention. These include, but are not limited to, eukaryotic hosts such as HeLa cells, CV-1 cell, COS cells, and Sf9 cells, as well as prokaryotic host such as *E. coli* and *B. subtilis*. The most preferred cells are those which do not normally express the particular reporter polypeptide or protein or which expresses the reporter polypeptide or protein at low natural level.

The host of the present invention may also be a yeast or other fungi. In yeast, a number of vectors containing constitutive or inducible promoters may be used. For a review see, *Current Protocols in Molecular Biology*, Vol. 2, Ed. Ausubel et al., Greene Publish. Assoc. & Wiley Interscience, Ch. 13 (1988); Grant et al. (1987) "Expression and Secretion Vectors for Yeast", *Methods Enzymol.* 153:516-544; Glover, *DNA Cloning*, Vol. II, IRL Press, Wash., D.C., Ch. 3 (1986); Bitter, *Heterologous Gene Expression in Yeast, Methods Enzymol.* 152:673-684 (1987); and *The Molecular Biology of the Yeast Saccharomyces*, Eds. Strathem et al., Cold Spring Harbor Press, Vols. I and II (1982).

The host of the invention may also be a prokaryotic cell such as *E. coli*, other enterobacteriaceae such as *Serratia marescans*, bacilli, various pseudomonads, or other prokaryotes which can be transformed, transfected, and/or infected.

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell.

Introduction of the recombinant construct into the host cell can be effected by calcium phosphate transfection, DEAE, dextran mediated transfection, or electroporation (Davis, L. et al., (1986) *Basic Methods in Molecular Biology*). The host cells containing one of polynucleotides of the invention, can be used in a conventional manner to produce the gene product encoded by the isolated fragment (in the case of an ORF).

Any host/vector system can be used to express one or more of the diversity strands of the present invention. These include, but are not limited to, eukaryotic hosts such as HeLa cells, CV-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety.

Various mammalian cell culture systems can also be employed to express recombinant protein.

Examples of mammalian expression systems include the COS-7 lines of monkey kidney fibroblasts, described by Gluzman (1981) *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine. The recombinant polypeptides encoded by a library of diversity strands can then be purified using affinity chromatography.

Microbial cells employed in expression of proteins can be disrupted by any convenient method, including freeze-thaw cycling, sonication, mechanical disruption, or use of cell lysing agents. A number of types of cells may act as suitable host cells for expression of the protein. Scopes ((1994) *Protein Purification: Principles and Practice*, Springer-Verlag, New York) provides a number of general methods for purifying recombinant (and non-recombinant) proteins. The method include, e.g., ion-exchange chromatography, size-exclusion chromatography, affinity chromatography, selective precipitation, dialysis, and hydrophobic interaction chromatography.

Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods. In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods.

Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules.

Monoclonal Antibody Production

Methods for generating monoclonal antibodies (mAbs) directed to a polypeptide encoded by a gene of a biomarker are described in U.S. Pat. Nos. RE 32,011, 4,902,614, 4,543, 439, 4,411,993 and 4,196,265 which are incorporated herein by reference; see also Monoclonal Antibodies, Hybridomas: A New Dimension in Biological Analyses, Kennett et al (eds.), Plenum Press (1980); and Antibodies. A Laboratory Manual, Harlow and Lane (eds.), Cold Spring Harbor Laboratory Press (1988), which also are incorporated herein by reference). Other techniques that enable the production of antibodies through recombinant techniques (e.g., techniques described by William D. Huse et al., Science, 246: 1275-1281

(1989); L. Sastry et al., Proc. Natl. Acad. Sci. USA, 86: 5728-5732 (1989); and Michelle Alting-Mees et al., Strategies in Molecular Biology, 3: 1-9 (1990) involving a commercial system available from Stratacyte, La Jolla, Calif.) may also be utilized to construct monoclonal antibodies.

In one preferred embodiment, monoclonal antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin ((1980) Proc. Natl. Acad. Sci. USA 77:4216-4220), used with a DHFR selectable marker, e.g., as described in Kaufman and Sharp ((1982) Mol. Biol. 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) Adv. Immunol. 51:1-84; Jefferis et al. (1998) Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Data Acquisition and Analysis of EST Sequences

The invention provides for EST sequences including "novel sequences", "novel expressed sequence tags (ESTs)" and "known sequences" including "known sequences with a function" and "known sequences with no known function".

The generated EST sequences are searched against available databases, including the "nt", "nr", "est", "gss" and "htg" databases available through NCBI to determine putative identities for ESTs matching to known genes or other ESTs. Relative EST frequency level can then be calculated using known methods. Functional characterization of ESTs with known gene matches are made according to any known method. Preferably, generated EST sequences are compared to the non-redundant GENBANK/EMBL/DDBJ and dbEST databases using the BLAST algorithm (8). A minimum value of $P=10^{-10}$ and nucleotide sequence identity >95%, where the sequence identity is non-contiguous or scattered, are required for assignments of putative identities for ESTs matching to known genes or to other ESTs. Construction of a non-redundant list of genes represented in the EST set is done with the help of Unigene, Entrez and PubMed at the National Center for Biotechnology Information (NCBI) site. Relative gene expression frequency is calculated by dividing the number of EST copies for each gene by the total number of ESTs analyzed.

Genes are identified from ESTs according to known methods. To identify novel genes from an EST sequence, the EST should preferably be at least 100 nucleotides in length, and more preferably 150 nucleotides in length, for annotation. Preferably, the EST exhibits open reading frame characteristics (i.e., can encode a putative polypeptide).

Because of the completion of the Human Genome Project, a specific EST which matches with a genomic sequence can be mapped onto a specific chromosome based on the chromosomal location of the genomic sequence. However, no function may be known for the protein encoded by the sequence and the EST would then be considered "novel" in a functional sense. In one aspect, the invention is used to identify a novel EST which is part of a larger known sequence for which no function is known is used to determine the function of a gene comprising the EST (e.g., such as the role of expression products produced by the gene in chondrogenesis and/or in a pathology affecting chondrocytes). Alternatively, or additionally, the EST can be used to identify an mRNA or polypeptide encoded by the larger sequence as a diagnostic or prognostic marker of chondrogenesis and/or of a pathology affecting chondrocytes.

Having identified an EST corresponding to a larger sequence, other portions of the larger sequence which comprises the EST can be used in assays to elucidate gene function, e.g., to isolate polypeptides encoded by the gene, to generate antibodies specifically reactive with these polypeptides, to identify binding partners of the polypeptides (receptors, ligands, agonists, antagonists and the like) and/or to detect the expression of the gene (or lack thereof) in chondrocytes in fetal, adult, normal, and/or diseased individuals.

In another aspect, the invention provides for nucleic acid sequences that do not demonstrate a "significant match" to any of the publicly known sequences in sequence databases at the time a query is done. Longer genomic segments comprising these types of novel EST sequences can be identified by probing genomic libraries, while longer expressed sequences can be identified in cDNA libraries and/or by performing polymerase extension reactions (e.g., RACE) using EST sequences to derive primer sequences as is known in the art. Longer fragments can be mapped to particular chromosomes by FISH and other techniques and their sequences compared to known sequences in genomic and/or expressed sequence databases and further functional analysis can be performed as described above.

Identified genes can be catalogued according to their putative function. Functional characterization of ESTs with known gene matches is preferably made according to the categories described by Hwang et al (Hwang D M, Dempsey A A, Wang R X, Rezvani M, Barrans J D, Dai K S, et al. A Genome-Based Resource for Molecular Cardiovascular Medicine: Toward a Compendium of Cardiovascular Genes. Circulation 1997;96:4146-203). The distribution of genes in each of the subcellular categories is indicative of the dynamic state of the tissue and will provide important insights into the osteoarthritis disease process.

Alternative methods for analyzing ESTs are also available. For example, the ESTs from each library may be assembled into contigs with sequence alignment, editing, and assembly programs such as PHRED and PHRAP (Ewing, et al., 1998, *Genome Res.* 3:175, incorporated herein; world wide web bozeman.genome.washington.edu/).Contig redundancy is reduced by clustering nonoverlapping sequence contigs using the EST clone identification number, which is common for the nonoverlapping $5^1$ and $3^1$ sequence reads for a single EST cDNA clone. In one aspect, the consensus sequence from each cluster is compared to the non-redundant GENBANK/EMBL/DDBJ and dbEST databases using the BLAST algorithm with the help of unigene, Entrez and PubMed at the NCBI site.

Known Nucleic Acid Sequences or ESTs and Novel Nucleic Acid Sequences or ESTs

An EST that exhibits a significant match (>65%, and preferably 90% or greater, identity) to at least one existing sequence in an existing nucleic acid sequence database is characterized as a "known" sequence according to the invention. Within this category, some known ESTs match to existing sequences which encode polypeptides with known function(s) and are referred to as a "known sequence with a function". Other "known" ESTs exhibit significant match to existing sequences which encode polypeptides of unknown function(s) and are referred to as a "known sequence with no known function".

EST sequences which have no significant match (less than 65% identity) to any existing sequence in the above cited available databases are categorized as novel ESTs. These novel ESTs are considered chondrocyte-specific since they are not matched to any other genes or ESTs derived from any other tissue. To identify a novel gene from an EST sequence, the EST is preferably at least 150 nucleotides in length. More preferably, the EST encodes at least part of an open reading frame, that is, a nucleic acid sequence between a translation initiation codon and a termination codon, which is potentially translated into a polypeptide sequence.

The invention provides for known and novel nucleic acid sequences that are uniquely expressed in mild osteoarthritic, moderate osteoarthritic, marked osteoarthritic and severe osteoarthritic cartilage. Tables 6 and 7 shows OA stage specific markers with GENBANK Accesion numbers and corresponding Protein Accession Numbers that are diagnostic for mild OA only (Tables 6a, 7a), moderate OA only (Table 6b), marked OA (Table 6c) and severe OA (Tables 6d, 7b) as identified in cartilage cDNA libraries using the methods according to the invention.

The invention also provides for known and novel nucleic acid sequences that are upregulated and downregulated in mild osteoarthritic and severe osteoarthritic cartilage.

Nucleic Acid Molecules of Potential Drug Markers

Many of the novel nucleic acid molecules of the present invention are differentially expressed between the various osteoarthritis disease states and are thus useful as potential drug targets or markers for the osteoarthritis disease process.

Microarrays

Construction of a Microarray

In one aspect, cDNAs generated from human cartilage cDNA libraries are arrayed on a microarray. Preferably, a microarray according to the invention comprises chondrocyte enriched or chondrocyte-specific genes and includes the whole spectrum of genes that are important in the osteoarthritis disease process.

Microarrays according to the invention may be used to show differential expression profiles between different developmental stages and osteoarthritis disease states for novel EST sequences. These novel EST sequences may be further characterized by cluster and alignment analyses to determine how many unique genes are represented by the novel EST sequences. The novel unique genes identified may provide a basis for identifying key markers in osteoarthritis disease progression and treatment.

In the subject methods, an array of nucleic acid members stably associated with the surface of a substantially solid support is contacted with a sample comprising probe nucleic acids under hybridization conditions sufficient to produce a hybridization pattern of complementary nucleic acid members/probe complexes in which one or more complementary nucleic acid members at unique positions on the array specifically hybridize to probe nucleic acids. The identity of probe nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

A microarray according to the invention comprises a plurality of unique nucleic acids attached to one surface of a solid support at a density exceeding 20 different nucleic acids/cm$^2$, wherein each of the nucleic acids is attached to the surface of the solid support in a non-identical pre-selected region. Each associated sample on the array comprises a nucleic acid composition, of known identity, usually of known sequence, as described in greater detail below. Any conceivable substrate may be employed in the invention.

In one embodiment, the nucleic acid attached to the surface of the solid support is DNA. In a preferred embodiment, the nucleic acid attached to the surface of the solid support is cDNA or RNA. In another preferred embodiment, the nucleic acid attached to the surface of the solid support is cDNA synthesized by polymerase chain reaction (PCR). Preferably, a nucleic acid member in the array, according to the invention, is at least 50 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length. In one embodiment, an array comprises at least 10 different nucleic acids attached to one surface of the solid support. In another embodiment, the array comprises at least 100 different nucleic acids attached to one surface of the solid support. In yet another embodiment, the array comprises at least 10,000 different nucleic acids attached to one surface of the solid support. In yet another embodiment, the array comprises at least 15,000 different nucleic acids attached to one surface of the solid support.

In the arrays of the invention, the nucleic acid compositions are stably associated with the surface of a solid support, where the support may be a flexible or rigid solid support. By "stably associated" is meant that each nucleic acid member maintains a unique position relative to the solid support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of probe nucleic acid sequences during the assay in which the array is employed. Generally, the amount of each nucleic acid member stably associated with the solid support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the solid support in a spot comprising an overall circular dimension, the diameter of the "spot" will generally range from about 10 to 5,000 µm, usually from about 20 to 2,000 µm and more usually from about 100 to 200 µm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as probe expression control nucleic acids and mismatch control nucleotides to monitor non-specific binding or cross-hybridization to a nucleic acid in the sample other than the probe to which the target is directed. Mismatch targets thus indicate whether a hybridization is specific or not. For example, if the probe is present, the perfectly matched targets should be consistently brighter than the mismatched targets. In addition, if all control mismatches are present, the mismatch targets are used to detect a mutation.

Solid Substrate

An array according to the invention comprises either a flexible or rigid substrate. A flexible substrate is capable of being bent, folded or similarly manipulated without breakage. Examples of solid materials which are flexible solid supports with respect to the present invention include membranes, e.g., nylon, flexible plastic films, and the like. By "rigid" is meant that the support is solid and does not readily bend, i.e., the support is not flexible. As such, the rigid substrates of the subject arrays are sufficient to provide physical support and structure to the associated nucleic acids present thereon under the assay conditions in which the array is employed, particularly under high throughput handling conditions.

The substrate may be biological, non-biological, organic, inorganic, or a combination of any of these, existing as particles, strands, precipitates, gels, sheets, tubing, spheres, beads, containers, capillaries, pads, slices, films, plates, slides, chips, etc. The substrate may have any convenient shape, such as a disc, square, sphere, circle, etc. The substrate is preferably flat or planar but may take on a variety of alternative surface configurations. The substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure.

In a preferred embodiment the substrate is flat glass or single-crystal silicon. According to some embodiments, the surface of the substrate is etched using well-known techniques to provide for desired surface features. For example, by way of formation of trenches, v-grooves, mesa structures, or the like, the synthesis regions may be more closely placed within the focus point of impinging light, be provided with reflective "mirror" structures for maximization of light collection from fluorescent sources, etc.

Surfaces on the solid substrate will usually, though not always, be composed of the same material as the substrate. Alternatively, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which are carboxyl, amino, hydroxyl, or the like. Most preferably, the surface will be optically transparent and will have surface Si—OH functionalities, such as are found on silica surfaces.

The surface of the substrate is preferably provided with a layer of linker molecules, although it will be understood that the linker molecules are not required elements of the invention. The linker molecules are preferably of sufficient length to permit nucleic acids of the invention and on a substrate to hybridize to other nucleic acid molecules and to interact freely with molecules exposed to the substrate.

Often, the substrate is a silicon or glass surface, (poly) tetrafluoroethylene, (poly)vinylidendifluoride, polystyrene, polycarbonate, a charged membrane, such as nylon 66 or nitrocellulose, or combinations thereof. In a preferred embodiment, the solid support is glass. Preferably, at least one surface of the substrate will be substantially flat. Preferably, the surface of the solid support will contain reactive groups, including, but not limited to, carboxyl, amino, hydroxyl, thiol, or the like. In one embodiment, the surface is optically transparent. In a preferred embodiment, the substrate is a poly-lysine coated slide or Gamma amino propyl silane-coated Corning Microarray Technology-GAPS or CMT-GAP2 coated slides.

Any solid support to which a nucleic acid member may be attached may be used in the invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Due to their flat surface, probe and hybridization reagents are minimized using glass slides. Slides also enable the targeted application of reagents, are easy to keep at a constant temperature, are easy to wash and facilitate the direct visualization of RNA and/or DNA immobilized on the solid support. Removal of RNA and/or DNA immobilized on the solid support is also facilitated using slides.

The particular material selected as the solid support is not essential to the invention, as long as it provides the described function. Normally, those who make or use the invention will select the best commercially available material based upon the economics of cost and availability, the expected application requirements of the final product, and the demands of the overall manufacturing process.

Spotting Method

In one aspect, the invention provides for arrays where each nucleic acid member comprising the array is spotted onto a solid support.

Preferably, spotting is carried out as follows. PCR products (~40 ul) of cDNA clones from osteoarthritis, fetal or normal cartilage cDNA libraries, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets are washed with 50 ul ice-cold 70% ethanol and centrifuged again for 30 minutes. The pellets are then air-dried and resuspended well in 20 ul 3×SSC or in 50% dimethylsulfoxide (DMSO) overnight. The samples are then spotted, either singly or in duplicate, onto slides using a robotic GMS 417 or 427 arrayer (Affymetrix, Ca).

The boundaries of the spots on the microarray may be marked with a diamond scriber (as the spots become invisible after post-processing). The arrays are rehydrated by suspending the slides over a dish of warm particle free ddH$_2$O for approximately one minute (the spots will swell slightly but will not run into each other) and snap-dried on a 70-80° C. inverted heating block for 3 seconds. Nucleic acid is then UV crosslinked to the slide (Stratagene, Stratalinker, 65 mJ—set display to "650" which is 650×100 uJ) or the array is baked at 80C for two to four hours prior to hybridization. The arrays are placed in a slide rack. An empty slide chamber is prepared and filled with the following solution: 3.0 grams of succinic anhydride (Aldrich) was dissolved in 189 ml of 1-methyl-2-pyrrolidinone (rapid addition of reagent is crucial); immediately after the last flake of succinic anhydride is dissolved, −21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. ddH$_2$O for 2 minutes, followed by plunging five times in 95% ethanol. The slides are then air dried by allowing excess ethanol to drip onto paper towels. The arrays are stored in the slide box at room temperature until use.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference, for teaching methods of polymer attachment.

Alternatively, spotting may be carried out using contact printing technology as is known in the art.

Nucleic Acid Microarrays

Any combination of the nucleic acid sequences generated from any of the chondrocyte cDNA libraries are used for the construction of a microarray. In one embodiment, the microarray is chondrocyte-specific and is anticipated to encompass the entire spectrum of genes that are important in the osteoarthritis disease process. A microarray according to the invention preferably comprises between 10 and 20,000 nucleic acid members, and more preferably comprises at least 5000 nucleic acid members. The nucleic acid members are known or novel nucleic acid sequences described herein, or any combination thereof. A microarray according to the invention is used to confirm differential gene expression profiles of genes that are specifically expressed at different cartilage development and osteoarthritis disease stages.

The invention also provides for a microarray comprising genes that are differentially expressed between normal and mild osteoarthritis patients to allow for the identification of early risk factors for osteoarthritis development. The invention also provides for a microarray for osteoarthritis diagnosis comprising one or more nucleic acid sequences that are differentially expressed between a normal individual and a patient diagnosed with mild, moderate, marked or severe osteoarthritis. Such arrays also may be used for prognostic methods to monitor a patient's response to therapy. Preferably, an array for osteoarthritis diagnosis comprises 10-20, 000 nucleic acid members and more preferably 50-15,000 nucleic acid members. In one embodiment, the above microarrays are used to identify a therapeutic agent that modulates the anabolic activity of a chondrocyte or changes (e.g., increases or decreases) the level of expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic.

The probe nucleic acid samples that are hybridized to and analyzed with a microarray of the invention are preferably from human cartilage. A limitation for this procedure lies in the amount of RNA available for use as a probe nucleic acid sample. Preferably, at least 1 microgram of total RNA is obtained for use according to this invention. This is advantageous because the amount of RNA in many cartilage biopsy samples is very minimal.

GENECHIP®

GeneChip® target arrays are manufactured through a unique and robust process—a combination of photolithography and combinatorial chemistry—that results in many of the arrays' powerful capabilities. With a calculated minimum number of synthesis steps, GeneChip technology produces arrays with hundreds of thousands of different targets packed at an extremely high density. This feature enables researchers to obtain high quality, genome-wide data using small sample volumes. Manufacture is scalable because the length of the targets, not their number, determines the number of synthesis steps required. This robust and automated production process yields arrays with highly reproducible properties, which reduces user set-up time by eliminating the need for individual labs to produce and test their own arrays.

Using technologies adapted from the semiconductor industry, GeneChip manufacturing begins with a 5-inch square quartz wafer. Initially the quartz is washed to ensure uniform hydroxylation across its surface. Because quartz is naturally hydroxylated, it provides an excellent substrate for the attachment of chemicals, such as linker molecules, that are later used to position the targets on the arrays.

The wafer is placed in a bath of silane, which reacts with the hydroxyl groups of the quartz, and forms a matrix of covalently linked molecules. The distance between these silane molecules determines the targets' packing density, allowing arrays to hold over 500,000 target locations, or features, within a mere 1.28 square centimeters. Each of these features harbors millions of identical DNA molecules. The silane film provides a uniform hydroxyl density to initiate target assembly. Linker molecules, attached to the silane matrix, provide a surface that may be spatially activated by light.

Target synthesis occurs in parallel, resulting in the addition of an A, C, T, or G nucleotide to multiple growing chains simultaneously. To define which oligonucleotide chains will receive a nucleotide in each step, photolithographic masks, carrying 18 to 20 square micron windows that correspond to the dimensions of individual features, are placed over the coated wafer. The windows are distributed over the mask based on the desired sequence of each target. When ultraviolet light is shone over the mask in the first step of synthesis, the exposed linkers become deprotected and are available for nucleotide coupling. Critical to this step is the precise alignment of the mask with the wafer before each synthesis step. To ensure that this critical step is accurately completed, chrome marks on the wafer and on the mask are perfectly aligned.

Once the desired features have been activated, a solution containing a single type of deoxynucleotide with a removable protection group is flushed over the wafer's surface. The nucleotide attaches to the activated linkers, initiating the synthesis process.

Although the process is highly efficient, some activated molecules fail to attach the new nucleotide. To prevent these "outliers" from becoming target with missing nucleotides, a capping step is used to truncate them. In addition, the side chains of the nucleotides are protected to prevent the formation of branched oligonucleotides.

In the following synthesis step, another mask is placed over the wafer to allow the next round of deprotection and coupling. The process is repeated until the targets reach their full length, usually 25 nucleotides.

Although each position in the sequence of an oligonucleotide can be occupied by 1 of 4 nucleotides, resulting in an apparent need for 25×4, or 100, different masks per wafer, the synthesis process can be designed to significantly reduce this requirement. Algorithms that help minimize mask usage calculate how to best coordinate target growth by adjusting synthesis rates of individual targets and identifying situations when the same mask can be used multiple times.

Once the synthesis is complete, the wafers are deprotected, diced, and the resulting individual arrays are packaged in flowcell cartridges. Depending on the number of target features per array, a single wafer can yield between 49 and 400 arrays.

The manufacturing process ends with a comprehensive series of quality control tests. Additionally, a sampling of arrays from every wafer is used to test the batch by running control hybridizations. A quantitative test of hybridization is also performed using standardized control targets.

After passing these rigorous tests, GeneChip target arrays are well prepared to help pursue ambitious goals ranging from the discovery of basic biological mechanisms to the development of new disease therapies.

The Human Genome U133 Set

The Human Genome U133 (HG-U133) Set, consisting of two GeneChip® arrays, contains almost 45,000 target sets representing more than 39,000 transcripts derived from approximately 33,000 well-substantiated human genes. This set design uses sequences selected from GenBank®, dbEST, and RefSeq.

The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release).

The HG-U133A Array includes representation of the RefSeq database sequences and target sets related to sequences previously represented on the Human Genome U95Av2 Array. The HG-U133B Array contains primarily target sets representing EST clusters.

15 K ChondroChip™ (Version 2b)

The ChondroChip™ version 2b is chondrocyte-specific microarray chip comprising 15000 novel and known EST sequences of the chondrocyte from chondrocyte-specific cDNA libraries.

Controls on the ChondroChip™

There are two types of controls used on microarrays. First, positive controls are genes whose expression level is invariant between different stages of investigation and are used to monitor:
  a) target DNA binding to the slide,
  b) quality of the spotting and binding processes of the target DNA onto the slide,
  c) quality of the RNA samples, and
  d) efficiency of the reverse transcription and fluorescent labelling of the probes.

Second, negative controls are external controls derived from an organism unrelated to and therefore unlikely to cross-hybridize with the sample of interest. These are used to monitor for:
  a) variation in background fluorescence on the slide, and
  b) non-specific hybridization.

There are currently 63 controls spots on the ChondroChip™ consisting of:

| Type | No. |
| --- | --- |
| Positive Controls: | 2 |
| Alien DNA | 12 |

-continued

| Type | No. |
| --- | --- |
| A. thaliana DNA | 10 |
| Spotting Buffer | 41 |

Protein Arrays

Polypeptides of the invention can be immobilized on a protein array. The protein array can be used as a diagnostic tool, e.g., to screen medical samples (such as biopsies, and the like) for the presence of the polypeptides encoded by one or more of the genes of a biomarker as defined herein. The protein array can also include antibodies as well as other ligands, e.g., that bind to the polypeptides encoded by the genes of a biomarker.

Methods of producing polypeptide arrays are described, e.g., in De Wildt et al. (2000) Nature Biotech. 18:989-994; Lueking et al. (1999) Anal. Biochem. 270:103-111; Ge (2000) Nuc. Acids Res. 28:e3; MacBeath and Schreiber (2000) Science 289:1760-1763; WO 01/40803, WO 99/51773A1 and U.S. Pat. No. 6,406,921. Polypeptides for the array can be spotted at high speed, e.g., using commercially available robotic apparati, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the polypeptide ligands can be grown on a filter in an arrayed format. Polypeptide production is induced, and the expressed antibodies are immobilized to the filter at the location of the cell. Information about the extent of binding at each address of the array can be stored as a profile, e.g., in a computer database.

In another example, the array is an array of polypeptides encoded by the genes of the invention, as described herein.

RT-PCR

In one aspect, nucleic acid sequences useful as nucleic acid targets or nucleic acid target probes of the invention can be made by amplifying RNA from cartilage using reverse transcription (RT) in combination with the polymerase chain reaction (PCR). RT-PCR methods are well-known to those skilled in the art.

Total RNA, or mRNA is used as a template and a primer specific to the transcribed portion of a gene of the invention is used to initiate reverse transcription. Primer design can be accomplished utilizing commercially available software (e.g. Primer Designer 1.0, Scientific Sofware etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the probe sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, Methods Enzymol., 155: 335, herein incorporated by reference.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10H PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Quantitative Real-Time RT PCR

Several techniques for detecting PCR products quantitatively without electrophoresis may be useful according to the invention (see for example PCR Protocols, A Guide to Methods and Applications, Innis et al., Academic Press, Inc. N.Y., (1990)).

One of these techniques, for which there are commercially available kits such as Taqman® (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The Taqman® system has the additional advantage of not requiring gel electrophoresis and allows for quantification when used with a standard curve.

A second technique useful for detecting PCR products quantitatively without electrophoresis, for which there is a commercially available kit such as QuantiTect™ SYBR® Green PCR (Qiagen, Valencia Calif.) is performed using SYBR® green as a fluorescent label which is incorporated into the PCR product during the PCR stage and produces a flourescense proportional to the amount of PCR product.

Both Taqman® and QuantiTect™ SYBR® systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Kits

The invention provides for kits for performing expression assays using the arrays of the present invention. Such kits according to the subject invention will at least comprise the arrays of the invention having associated nucleic acid members and packaging means therefore. The kits may further comprise one or more additional reagents employed in the various methods, such as: 1) primers for generating test nucleic acids; 2) dNTPs and/or rNTPs (either premixed or separate), optionally with one or more uniquely labeled dNTPs and/or rNTPs (e.g., biotinylated or CY3 or CY5 tagged dNTPs); 3) post synthesis labeling reagents, such as chemically active derivatives of fluorescent dyes; 4) enzymes, such as reverse transcriptases, DNA polymerases, and the like; 5) various buffer mediums, e.g., hybridization and washing buffers; 6) labeled probe purification reagents and components, like spin columns, etc.; and 7) signal generation and detection reagents, e.g., streptavidin-alkaline phosphatase conjugate, chemifluorescent or chemiluminescent substrate, and the like.

Use of a Microarray

Nucleic acid arrays according to the invention can be used in high throughput techniques that can assay a large number of nucleic acids in a sample comprising one or more target nucleic acid sequences. The arrays of the subject invention find use in a variety of applications, including gene expression analysis, diagnosis of osteoarthritis and prognosis of osteoarthritis, monitoring a patient's response to therapy, drug screening, and the like.

In one aspect, the arrays of the invention are used in, among other applications, differential gene expression assays. For example, arrays are useful in the differential expression analysis of: (a) diagnosis of disease and/or disease stage; (b) developing cartilage (e.g., fetal cartilage); (c) chondrocyte responses to external or internal stimuli; (d) cartilage/chondrocyte response to treatment; (e) cartilage tissue engineering; (f) pharmacogenomics; and the like.

For example, arrays useful in the invention can include sequences which demonstrate increased or decreased expression in patient's having osteoarthritis as compared to normal individuals. More particularly, an array useful in accordance with the invention include sequences which demonstrate increased or decreased expression in patients identified as having a particular stage of progression of the disease, for example mild osteoarthritis but not demonstrating increased or decreased expression in another stage of progression of the disease, for example severe osteoarthritis.

Arrays can be made using at least one, more preferably a majority of these sequences, as a means of diagnosing osteoarthritis, or for purposes of monitoring efficacy of treatment and of osteoarthritis.

For example an array of the invention can be used to diagnose an individual having osteoarthritis by hybridizing a sample complementary to a patient's RNA to an array comprising sequences identified as having increased or decreased expression, and comparing the level of intensity of hybridization as between this sample and a sample complementary to RNA isolated from normal individuals to a similar or identical second array.

Similarly, an array of the invention can be used to monitor the efficacy of treatment in patients who have osteoarthritis by hybridizing a sample complementary to a patient's RNA, wherein the patient has been treated so as to reduce the progression of osteoarthritis, and determining the intensity of the hybridization as compared with the intensity of hybridization of a standard sample hybridized to another array of the invention.

Additionally, an array of the invention can be utilized to identify an agent that increases or decreases the expression of a polynucleotide sequence of the invention by incubating a chondrocyte derived from a normal individual with a candidate agent, wherein said chondrocyte is isolated from a cartilage sample obtained from said normal individual less than 14 hours post-mortem; hybridizing a sample complementary to a patient's RNA to an array of the invention, and hybridizing a sample useful as a standard to another array of the invention and comparing the intensity of expression between corresponding unique positions on the arrays.

The choice of a standard sample would be well understood by a person skilled in the art, and would include a sample complementary to RNA isolated from one or more normal individuals, wherein a normal individual is an individual not suffering from osteoarthritis. A standard sample would include a sample complementary to RNA isolated from chondrocytes.

Probe Preparation

The probes for the microarrays according to the invention are preferably derived from human cartilage.

A probe nucleic acid is capable of binding to a nucleic acid target or nucleic acid member of complementary sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable probe nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid probes used herein are preferably derived from human cartilage. Preferably, the probes are nucleic acids derived from human cartilage extracts. Nucleic acids can be single- or double-stranded DNA, RNA, or DNA-RNA hybrids synthesized from human cartilage mRNA extracts using methods known in the art, for example, reverse transcription or PCR.

In the simplest embodiment, such a nucleic acid probe comprises total mRNA or a nucleic acid sample corresponding to mRNA (e.g., cDNA) isolated from cartilage samples. In another embodiment, total mRNA is isolated from a given sample using, for example, an acid guanidinium-phenol-chloroform extraction method and polyA+mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the probe nucleic acid sample prior to hybridization. One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include targets specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989, *Genomics*, 4:560; Landegren, et al., 1988, *Science*, 241:1077 and Barringer, et al., 1990, *Gene*, 89:117, transcription amplification (Kwoh, et al., 1989, *Proc. Natl. Acad. Sci. USA*, 86: 1173), and self-sustained sequence replication (Guatelli, et al., 1990, *Proc. Nat. Acad. Sci. USA*, 87:1874).

In a particularly preferred embodiment, the probe nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, *Proc. Natl. Acad. Sci. USA*, 87: 1663-1667 who demonstrate that in vitro amplification according to this method preserves the relative frequencies of the various RNA transcripts. Moreover, Eberwine et al. *Proc. Natl. Acad. Sci. USA*, 89: 3010-3014 provide a protocol that uses two rounds of amplification via in vitro transcription to achieve greater than $10^6$ fold amplification of the original starting material thereby permitting expression monitoring even where biological samples are limited.

Labeling of Target or Nucleic Acid Probe

Either the target or the probe can be labeled.

Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, TEXAS RED, rhodamine, green fluorescent protein, and the like), radiolabels (e.g., $^3$H, $^{125}$I, 35S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In a preferred embodiment, the fluorescent modifications are by cyanine dyes e.g. Cy-3/Cy-5 dUTP, Cy-3/Cy-5 dCTP (Amersham Pharmacia) or alexa dyes (Khan,et al., 1998, *Cancer Res.* 58:5009-5013).

In a preferred embodiment, the two probe samples used for comparison are labeled with different fluorescent dyes which produce distinguishable detection signals, for example, probes made from normal cartilage are labeled with CY5 and probes made from mild osteoarthritis cartilage are labeled with CY3. The differently labeled probe samples are hybridized to the same microarray simultaneously. In a preferred embodiment, the labeled probes are purified using methods known in the art, e.g., by ethanol purification or column purification.

In a preferred embodiment, the probe will include one or more control molecules which hybridize to control targets on the microarray to normalize signals generated from the microarray. Preferably, labeled normalization probes are nucleic acid sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other targets in the array are divided by the signal (e.g., fluorescence intensity) from the control targets, thereby normalizing the measurements.

Preferred normalization probes are selected to reflect the average length of the other probes present in the sample, however, they are selected to cover a range of lengths. The normalization control(s) also can be selected to reflect the (average) base composition of the other targets in the array, however, in a preferred embodiment, only one or a few normalization targets are used and they are selected such that they hybridize well (i.e., have no secondary structure and do not self hybridize) and do not match any probe molecules.

Normalization targets are localized at any position in the array or at multiple positions throughout the array to control for spatial variation in hybridization efficiency. In a preferred embodiment, normalization controls are located at the s or edges of the array as well as in the middle.

Hybridization Conditions

Nucleic acid hybridization involves providing a denatured target nucleic acid member and probe nucleic acid under conditions where the probe nucleic acid member and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., *Laboratory Techniques in Biochemistry and Molecular Biology*, Vol. 24: *Hybridization With Nucleic acid Probes*, P. Tijssen, ed. Elsevier, N.Y., (1993)).

Following hybridization, non-hybridized labeled or unlabeled nucleic acid is removed from the support surface, conveniently by washing, thereby generating a pattern of hybridized probe nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled probe nucleic acids to obtain a count or absolute value of the copy number of each end-labeled probe that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two cartilage samples to be compared, where each sample is labeled with a different fluorescent dye.

Each element of the microarray is scanned for the first fluorescent color. The intensity of the fluorescence at each array element is proportional to the expression level of that gene in the sample.

The scanning operation is repeated for the second fluorescent label. The ratio of the two fluorescent intensities provides a highly accurate and quantitative measurement of the relative gene expression level in the two tissue samples.

In a preferred embodiment, fluorescence intensities of immobilized probe nucleic acid sequences were determined from images taken with a custom confocal microscope equipped with laser excitation sources and interference filters appropriate for the CY3 and CY5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each probe are as described (Khan, et al., 1998, *Cancer Res.* 58:5009-5013. Chen, et al., 1997, *Biomed. Optics* 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy 3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of CY5 to CY3 is calculated. A liner regression approach is used for normalization and assumes that a scatter plot of the measured CY5 versus CY3 intensities should have a scope of one. The average of the ratios is calculated and used to rescale the data and adjust the slope to one. A post-normalization cutoff of greater than 1.0 fold up- or down-regulation is used to identify differentially expressed genes.

Following detection or visualization, the hybridization pattern is used to determine quantitative information about the genetic profile of the labeled probe nucleic acid sample that was contacted with the array to generate the hybridization pattern, as well as the physiological source from which the labeled probe nucleic acid sample was derived. By "genetic profile" is meant information regarding the types of nucleic acids present in the sample, e.g., such as the types of genes to which they are complementary, and/or the copy number of each particular nucleic acid in the sample. From this data, one can also derive information about the physiological source from which the probe nucleic acid sample was derived, such as the types of genes expressed in the tissue or cell which is the physiological source of the target, as well as the levels of expression of each gene, particularly in quantitative terms.

Diagnostic or Prognostic Tests

The invention also provides for diagnostic tests for detecting osteoarthritis. The invention also provides for prognostic tests for monitoring a patient's response to therapy.

According to the method of the invention, mild, moderate, marked or severe osteoarthritis is detected by obtaining a cartilage sample from a patient. A sample comprising nucleic acid corresponding to RNA (i.e., RNA or cDNA) is prepared from the patient cartilage sample. The sample comprising nucleic acid corresponding to RNA is hybridized to an array comprising a solid substrate and a plurality of nucleic acid members, where at least one member is differentially expressed in cartilage isolated from a patient diagnosed with mild, moderate, marked or severe osteoarthritis, as compared to a "normal individual", according to the invention. According to this diagnostic test, differential hybridization of RNA of the sample as compared to a normal control is indicative of disease.

A patient response to therapy is monitored by using a prognostic test according to the invention. In one aspect, a prognostic test according to the invention comprises obtaining a cartilage sample from a patient prior to treatment, during the course of treatment and after treatment. Preferably, the patient is treated for at least 12 hours before a sample is taken. A sample comprising nucleic acid corresponding to RNA (i.e., RNA or cDNA) is prepared from the patient cartilage samples. The samples comprising nucleic acid corresponding to RNA are hybridized to an array comprising a solid substrate and a plurality of nucleic acid members, wherein at least one member is differentially expressed in cartilage isolated from a patient diagnosed with mild, moderate, marked or severe osteoarthritis, as compared to a normal individual, according to the invention. Arrays are selected in accordance with the diagnostic state of the patient whose treatment is being monitored. According to this prognostic test, differential hybridization of the samples comprising nucleic acid corresponding to RNA isolated prior to and after treatment to one or more nucleic acid members on the array is indicative of an effective treatment. Preferably, gene expression profiles in patients being treated changes to resemble more closely gene expression profiles in patients with less severe forms of the disease or more preferably more closely resembles gene expression profiles in normal patients. The extent of change in a gene expression profile can be further correlated with various therapeutic endpoints such as a decrease in the severity and/or occurrence of one or more symptoms associated with the disease.

Therapeutic Agents

A useful therapeutic agent according to the invention can increase or decrease the anabolic and/or the catabolic activity of a chondrocyte. Preferably, a therapeutic agent can increase or decrease the anabolic and/or catabolic activity of a chondrocyte by greater than 1.0-fold, more preferably, 1.5-5-fold, and most preferably, 5-100-fold, as compared to an untreated chondrocyte.

In one embodiment, a therapeutic agent changes (e.g., increases or decreases) the level of expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic. Preferably, a therapeutic agent causes a change in the level of expression of a nucleic acid sequence or increase or decrease in the expression of a nucleic acid sequence that is differentially expressed in a chondrocyte derived from any of the following chondrocyte disease or developmental stages: fetal, normal, mild osteoarthritic, moderate osteoarthritic, marked osteoarthritic and severe osteoarthritic, where the change is greater than 1.0-fold, more preferably 1.5-5-fold, and most preferably 5-100-fold, more or less than the level of expression in the absence of a candidate therapeutic agent.

In another embodiment, a therapeutic agent according to the invention can ameliorate at least one of the symptoms and/or changes associated with osteoarthritis including cartilage degeneration, or pain, swelling, weakness and/or loss of functional ability in the afflicted joints, associated with cartilage degeneration.

The candidate therapeutic agent may be a synthetic compound, or a mixture of compounds, or may be a natural product (e.g. a plant extract or culture supernatant).

Candidate therapeutic agents or compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Monitoring Drug Efficacy

The drug efficacy can be monitored by comparing the expression profile of one or more differentially expressed genes between any two cartilage samples from one stage of osteoarthritis as compared with a different stages of osteoarthritis. Cartilage samples were taken from an individual during or after the treatment of a candidate drug as described herein above. As a comparison, cartilage samples were also taken from either the same individual prior to the treatment of the drug or from another individual not treated with the drug. Nucleic acids were extracted from the samples as described and hybridized to an array of the present invention. If one or more nucleic acid members on the array were found to be expressed at different levels in the sample taken from the treated individual compared to the sample taken from the untreated individual, it was indicative of the efficacy of the drug for the treatment of osteoarthritis. Follow-up analysis (e.g., by PCR or Western blot analysis) were then followed to verify the expression differences.

Dosage and Administration

Therapeutic agents of the invention are administered to a patient, preferably in a biologically compatible solution or a pharmaceutically acceptable delivery vehicle, by ingestion, injection, inhalation or any number of other methods routine in the art. The dosages administered will vary from patient to patient. A "therapeutically effective dose" is determined, for example, by the level of enhancement of function (e.g., increased or decreased chondrocyte anabolic activity, or an increase or decrease in the expression of at least one nucleic acid sequence that is differentially expressed in a chondrocyte derived from any of the following chondrocyte disease or developmental stages: fetal, normal, mild osteoarthritic, moderate osteoarthritic, marked osteoarthritic or severe osteoarthritic).

A therapeutic agent according to the invention is administered in a single dose. This dosage may be repeated daily, weekly, monthly, yearly, or as considered appropriate by the treating physician.

Pharmaceutical Compositions

The invention provides for compositions comprising a therapeutic agent according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which is used pharmaceutically.

Pharmaceutical compositions for oral administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use are obtained through a combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which are used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and are formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a therapeutic agent of the invention formulated in a acceptable carrier have been prepared, they are placed in an appropriate container and labeled for treatment of an indicated condition with information including amount, frequency and method of administration.

Efficacy of Osteoarthritis Therapy Using a Defined Therapeutic Agents

The efficacy of the therapy using any of the therapeutic agents according to the invention is determined by a medical practitioner. This determination may be related to alleviating osteoarthritis symptoms such as pain, swelling, weakness and loss of functional ability in the afflicted joint(s), and/or criteria for osteoarthritis diagnosis and staging described in Marshall (1996, supra).

The above disclosure generally describes the present invention. A more complete understanding can be obtained by reference to the following specific examples, which are provided herein for purposes of illustration only and are not intended to limit the scope of the invention.

EXAMPLES

The examples below are non-limiting and are merely representative of various aspects and features of the present invention

Example 1

RNA Extraction, cDNA Library Construction and EST Analysis

Normal cartilage was obtained from the donor program of Department of Orthopaedics and Rehabilitation, University of Miami. OA cartilage samples were obtained from either areas of very early cartilage degeneration (mild) or from sites of moderate, marked or severe cartilage degeneration during either arthroscopic knee surgery or total knee replacement. OA severity was graded according to the system described by Marshall (Marshall K W. J Rheumatol, 1996:23(4) 582-85). Briefly, each of the six knee articular surfaces was assigned a cartilage grade with points based on the worst lesion seen on each particular surface. Grade 0 is normal (0 points), Grade I cartilage is soft or swollen but the articular surface is intact (1 point). In Grade II lesions, the cartilage surface is not intact but the lesion does not extend down to subchondral bone (2 points). Grade III damage extends to subchondral bone but the bone is neither eroded nor ebumated (3 points). In Grade IV lesions, there is ebumation of or erosion into bone (4 points). A global OA score is calculated by summing the points from all six cartilage surfaces. If there is any associated pathology, such as meniscus tear, an extra point will be added to the global score. Based on the total score, each patient is then categorized into one of four OA groups: mild (1-6), moderate (7-12), marked (13-18), and severe (>18).

Total RNA from cartilage was extracted using TRIzol® reagent (GIBCO). cDNA libraries were constructed into λTriplEx2 vector through a PCR-based method, using SMART (Switching Mechanism At 5' end of RNA Transcript) cDNA Library Construction Kit (Clontech) as described above. Phage plaques were randomly picked and positive inserts were identified by PCR. Agarose gel electrophoresis was used to assess the presence and purity of inserts. PCR product was then subjected to automated DNA sequencing with a 5'vector-specific forward primer and sequenced by ABI PRISM 377 DNA sequencer (Perkin Elmer) and ABI PRISM 3700 DNA Analyzer (Applied Biosystems). ESTs were obtained from each of the cDNA libraries and sequenced.

Large-scale Sequencing of cDNA Inserts

From the amplified λ ZAP Express library, phage plaques were plated at a density of 200-500 pfu/150 mm plate onto *Escherichia coli* XL1-blue MRF' lawn with IPTG/X-gal for color selection. Plaques were picked into 75 ul suspension media buffer (100 mM NaCl, 10 mM $MgSO_4$, 1 mM Tris, pH7.5, 0.02% gelatin). Phage elutes (5 ul) were used for PCR reactions (50 ul total volume) with 125 umol/L of each dNTP (Pharmacia), 10 pmol each of modified T3 (5'-GC-CAAGCTCGAAATTAACCCTCACTAAAG GG-3' (SEQ ID NO: 19)) and T7 (5'-CCAGTGAATTGTAATACGACT-CACTATAGGGCG-3' (SEQ ID NO: 20)) primers, and 2 U of Taq DNA polymerase (Pharmacia). Reactions were cycled in a DNA Thermal Cycler (Perkin-Elmer) [denaturation at 95° C. for 5 minutes, followed by 30 cycles of amplification (94° C., 45 seconds; 55° C., 30 seconds; 72° C., 3 minutes) and a terminal isothermal extension (72° C., 3 minutes)]. Agarose gel electrophoresis was used to assess the presence and purity of inserts. PCR products are subjected to DNA sequencing reactions using specific primers, BigDye™ Terminator Cycle Sequencing v2.0 Ready Reaction (PE Biosystems), Tris MgCl buffer and water in a thermocycler. Sequencing reactions were incubated at 94° C. for 2 minutes, followed by 25 cycles of 94° C., 30 seconds; 55° C., 20 seconds; and 72° C., 1 minute; and 15 cycles of 94° C., 30 seconds; and 72° C. for 1 minute; and 72° C. for 5 minues. Reactions were then put on hold at 4° C. until purified through methods well known in the prior art (i.e. column purification or alcohol precipitation). Automated sequencing was carried out with a PE Biosystems ABI Prism 3700 DNA Analyzer.

Sequences were manually edited or edited using Sequencher software (GeneCodes). All edited EST sequences were compared to the non-redundant GENBANK/EMBL/DDBJ and dbEST databases using the BLAST algorithm (8). A minimum value of $P=10^{-10}$ and nucleotide sequence identity >95% were required for assignments of putative identities for ESTs matching to known genes or to other ESTs. Construction of a non-redundant list of genes represented in the EST set was done with the help of Unigene, Entrez and PubMed at the National Center for Biotechnology Information (NCBI) site.

Example 2

Microarray Construction

Microarrays using ESTs isolated from the four cDNA libraries as described above were created.

PCR products (~40 ul) of cDNA clones from OA cartilage cDNA libraries as described above were utilized in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets were washed with 50 ul ice-cold 70% ethanol and centrifuged again for 30 minutes. The pellets are then air-dried and resuspended well in 50% dimethylsulfoxide (DMSO) or 20 ul 3×SSC overnight. The samples are then deposited either singly or in duplicate onto Gamma Amino Propyl Silane (Corning CMT-GAPS or CMT-GAP2, Catalog No. 40003, 40004) or polylysine-coated slides (Sigma Cat. No. P0425) using a robotic GMS 417 or 427 arrayer (Affymetrix, Calif.). The boundaries of the DNA spots on the microarray are marked with a diamond scriber. The invention provides for arrays where 10-20,000 PCR products are spotted onto a solid support to prepare an array.

The arrays are rehydrated by suspending the slides over a dish of warm particle free $ddH_2O$ for approximately one minute (the spots will swell slightly but not run into each other) and snap-dried on a 70-80° C. inverted heating block for 3 seconds. DNA is then UV crosslinked to the slide (Stratagene, Stratalinker, 65 mJ—set display to "650" which is 650×100 uJ) or baked at 80C for two to four hours. The arrays are placed in a slide rack. An empty slide chamber is prepared and filled with the following solution: 3.0 grams of succinic anhydride (Aldrich) is dissolved in 189 ml of 1-methyl-2-pyrrolidinone (rapid addition of reagent is crucial); immediately after the last flake of succinic anhydride dissolved, 21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. $ddH_2O$ for 2 minutes, followed by plunging five times in 95% ethanol. The slides are then air dried by allowing excess ethanol to drip onto paper towels. The arrays are then stored in the slide box at room temperature until use.

Example 3

Target Nucleic Acid Preparation and Hybridization Using Constructed Arrays

Preparation of Fluorescent DNA Probe from mRNA

Fluorescently labeled target nucleic acid samples are prepared for analysis with an array of the invention.

2 µg Oligo-dT primers are annealed to 2 ug of mRNA isolated from a cartilage sample from patient diagnosed with osteoarthritis as described above in a total volume of 15 ul, by heating to 70° C. for 10 min, and cooled on ice. The mRNA is reverse transcribed by incubating the sample at 42° C. for 1.5-2 hours in a 100 µl volume containing a final concentration of 50 mM Tris-HCl (pH 8.3), 75 mM KCl, 3 mM MgCl2, 25 mM DTT, 25 mM unlabeled dNTPs, 400 units of Superscript II (200 U/uL, Gibco BRL), and 15 mM of CY3 or CY5 (Amersham). RNA is then degraded by addition of 15 µl of 0.1N NaOH, and incubation at 70° C. for 10 min. The reaction mixture is neutralized by addition of 15 µl of 0.1N HCL, and the volume is brought to 500 µl with TE (10 mM Tris, 1 mM EDTA), and 20 µg of Cot1 human DNA (Gibco-BRL) is added.

The labeled target nucleic acid sample is purified by centrifugation in a Centricon-30 micro-concentrator (Amicon). If two different target nucleic acid samples (e.g., two samples derived from different patients) are being analyzed and compared by hybridization to the same array, each target nucleic acid sample is labeled with a different fluorescent label (e.g., CY3 and CY5) and separately concentrated. The separately concentrated target nucleic acid samples (CY3 and CY5 labeled) are combined into a fresh centricon, washed with 500 µl TE, and concentrated again to a volume of less than 7 µl. 1 µL of 10 µg/µl polyA RNA (Sigma, #P9403) and 1 µl of 10 µg/ul tRNA (Gibco-BRL, #15401-011) is added and the volume is adjusted to 9.5 µl with distilled water. For final target nucleic acid preparation 2.1 µl 20×SSC (1.5M NaCl, 150 mM NaCitrate (pH8.0)) and 0.35 µl 10%SDS is added.

Hybridization Using the ChondroChip™ Constructed Array

Labeled nucleic acid is denatured by heating for 2 min at 100° C., and incubated at 37° C. for 20-30 min before being placed on a nucleic acid array under a 22 mm×22 mm glass cover slip. Hybridization is carried out at 65° C. for 14 to 18 hours in a custom slide chamber with humidity maintained by a small reservoir of 3×SSC. The array is washed by submersion and agitation for 2-5 min in 2×SSC with 0.1%SDS, followed by 1×SSC, and 0.1×SSC. Finally, the array is dried by centrifugation for 2 min in a slide rack in a Beckman GS-6 tabletop centrifuge in Microplus carriers at 650 RPM for 2 min.

Example 4

Target Nucleic Acid Preparation and Hybridization Using Affymetrix® U133A Microarray Preparation of Biotinylated cDNA Biotinylated DNA probes are prepared from total mRNA using the Affymetrix® Eukaryotic Target Preparation protocol.

More particularly 2 µg T7 Oligo-dT primers (5 uM) are annealed to 2 ug of mRNA isolated from a cartilage sample from patient diagnosed with osteoarthritis, as described above, in a total volume of 2 ul, by heating to 70° C. for 6 min, and cooled on ice. The mRNA is reverse transcribed by incubating the sample at 42° C. for 1 hour in a 20 µl volume containing a final concentration of 1× first stand buffer (Affymetrix®), 20 mM DTT, 1.25 mM unlabeled dNTPs, 100 units of Superscript II (200 U/uL, Gibco BRL). Second strand synthesis is performed by incubating at 16° C. for 2 hours the first strand reaction in a final concentration of 1× Second Strand Reaction Buffer (Affymetrix®) 200 uM dNTPs, 10U E. Coli DNA Ligase; 40U E. Coli DNA Polymerase 1 and 2U of E. Coli Rnase H (Affymetrix®) to a final volume of 150 µl. 2 µl (10U) of T4 DNA Polymerase is added and the reaction reincubated for an additional 5 minutes. Reaction is stopped with the addition of 10 µl of 0.5M EDTA. cDNA is purified utilizing the Affymetrix® GeneChip Sample Cleanup Module.

cRNA is created and labelled by incubating the template cDNA with 1×HY Reaction Buffer; 1× biotin-lableled ribonucleotides, 1×DTT; 1× Rnase Inhibitor Mix and 1×T7 RNA polymerase (Affymetrix®) and the reaction incubated at 37° C. for 4-5 hours.

The labeled cRNA nucleic acid sample is purified using the Affymetrix® GeneChip Sample Cleanup Module. CRNA is fragmented in accordance with the Affymetrix® protocol prior to hybridization.

Hybridization Using the Affymetrix® U133A Array

Hybridization is performed in accordance with the Affymetrix® Eukaryotic Target Preparation protocol. Following hybridization of an array with one or more labeled target nucleic acid samples, arrays are scanned immediately using a GeneChip Fluidics Station 450 and Genechip Scanner (Affymetrix®).

Example 5

Detection of OA Biomarkers (Nucleic Acids) Specific for Mild OA or Severe OA This example demonstrates the use of the claimed invention to detect either mild OA specific or severe OA specific biomarkers utilizing the ChondroChip™ as demonstrated in Tables 1-4.

Data Analysis was performed on RNA isolated from cartilage samples of normal individuals, individuals having mild osteoarthritis, and individuals having severe osteoarthritis. OA severity was graded according to the system described by Marshall (Marshall K W. J Rheumatol, 1996:23(4) 582-85) as described herein.

Sample RNA from either normal, mild or severe OA cartilage was labelled with fluorescent dye CY3 or CY5, and Universal Human Reference RNA (Stratagene, Product# 740000) labelled with the remaining fluorescent dye and normalized intensities for each sample RNA determined having taken into account intensity differences as a result of the use of the different dyes. Analysis was performed using GeneSpring 4.1.5 and genes demonstrating a stage specific difference in expression intensity of greater than 2 fold when compared to either the intensity from the normal cartilage or any other stage specific cartilage RNA were identified.

Tables 1-4 provide those genes identified as unique to either mild or severe OA.

---

Lengthy table referenced here

US07452667-20081118-T00001

Please refer to the end of the specification for access instructions.

Lengthy table referenced here

US07452667-20081118-T00002

Please refer to the end of the specification for access instructions.

Lengthy table referenced here

US07452667-20081118-T00003

Please refer to the end of the specification for access instructions.

Lengthy table referenced here

US07452667-20081118-T00004

Please refer to the end of the specification for access instructions.

Lengthy table referenced here

US07452667-20081118-T00005

Please refer to the end of the specification for access instructions.

Example 6

Detection of OA Biomarkers Specific for Mild OA, Marked OA, Moderate OA or Severe OA This example demonstrates the use of the claimed invention to detect stage specific OA biomarkers utilizing the ChondroChip™ or the Affymetrix® U133A as demonstrated in Table 6 and Table 7 respectively.

Data Analysis was performed on RNA isolated from cartilage samples of normal individuals, individuals having mild osteoarthritis, individuals having moderate osteoarthritis, individuals having marked osteoarthritis and individuals having severe osteoarthritis. OA severity was graded according to the system described by Marshall (Marshall K W. J Rheumatol, 1996:23(4) 582-85) as described herein.

Sample RNA from either normal, mild, moderate, marked or severe OA cartilage was labelled with fluorescent dye CY3 or CY5, and Universal Human Reference RNA (Stratagene, Product# 740000) labelled with the remaining fluorescent dye and normalized intensities for each sample RNA determined having taken into account intensity differences as a result of the use of the different dyes. Analysis was performed using GeneSpring 6.0. Each disease group was compared to the normal samples: mild/normal, moderate/normal, marked/normal and severe/normal. A cut-off p-value for statistical significance was 0.05. Statistical tests: non-parametric (Wilcoxon-Mann-Witney or Kruskal-Wallis) or parametric, variances not assumed equal (Welch ANOVA) (Glantz S A. Primer of Biostatistics. 5th ed. New York, USA: McGraw-Hill Medical Publishing Division, 2002). Genes were identified as disease group associated genes from the 14,967 genes on the 15K ChondroChip™ which demonstrated a statistically significant difference when compared with the normal control. ("OA list"). Genes wherein the expression level correlated with other parameters, such as age, gender, hybridization date and slide batch, when such parameters could be reviewed, were removed from the OA list. The OA list generated from each stage specific sample were compared and genes identified which were unique for each specific stage.

Lengthy table referenced here

US07452667-20081118-T00006

Please refer to the end of the specification for access instructions.

Lengthy table referenced here

US07452667-20081118-T00007

Please refer to the end of the specification for access instructions.

Lengthy table referenced here

US07452667-20081118-T00008

Please refer to the end of the specification for access instructions.

Lengthy table referenced here

US07452667-20081118-T00009

Please refer to the end of the specification for access instructions.

Lengthy table referenced here

US07452667-20081118-T00010

Please refer to the end of the specification for access instructions.

Lengthy table referenced here

US07452667-20081118-T00011

Please refer to the end of the specification for access instructions.

Example 8

Detection of OA Biomarkers (Proteins) Specific for Mild OA or Severe OA

This example demonstrates the use of the invention to diagnose mild or severe osteoarthritis by detecting differential gene expression in samples taken from patients with OA as compared to samples taken from healthy patients.

Cartilage samples are taken from patients who are clinically diagnosed with mild or severe osteoarthritis as defined herein. Gene expression profiles are then analyzed and compared to profiles from patients unaffected by OA. In each case, the diagnosis of osteoarthritis is corroborated by a skilled Board certified physician.

Total cellular protein from a cartilage sample taken from each patient is first isolated and labelled using the BD Clontech Protein Extraction and labelling kit (Catalogue #K1848-1 or #631786). Briefly, the Extraction Protocol consists of three main steps: mechanically disrupting the cells, solubilizing the cells, and centrifuging the extract The process may start with a cell pellet or frozen tissue and may use any method of mechanical disruption—French press, sonication, mincing, or grinding. Once disrupted, the sample is solubilized by adding the Extraction/Labeling Buffer (1:20 w/v). Because the Buffer is formulated for labeling with N-hydroxysuccinimide (NHS)-ester dyes (e.g. CY3 and CY5 dyes), it does not contain any protease inhibitors or reducing agents that would compete for reaction with the dye. After extraction, the sample is centrifuged to pellet insoluble material such as chromosomal DNA. The soluble extract is then labelled with CY3 and CY5 Fluorescent Dyes (monofunctional NHS-esters). The labelled proteins are then incubated with an array of monoclonal antibodies which are directed to full length polypeptides encoded by the genes described in Tables 1, 3, 6a, 7a (mild OA) or Tables 2, 4, 6d or 7b (Severe OA). Detection of specific binding to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the mild OA specific of severe OA-specific genes in the samples from patients with mild and severe osteoarthritis respectively as compared to healthy patients is determined by statistical analysis using the Wilcox Mann Whitney rank sum test (Glantz S A. Primer of Biostatistics. 5th ed. New York, USA: McGraw-Hill Medical Publishing Division, 2002). Differential expression of each of the genes described in Tables 1, 3, 6a, 7a is diagnostic for mild osteoarthritis. Differential expression of each of the genes described in Tables 2, 4, 6d or 7b is diagnostic of severe OA.

Example 9

Monitoring Drug Efficacy

The drug efficacy can be monitored by comparing the expression profile of one or more differentially expressed genes between any two cartilage samples from normal and different stages of osteoarthritic. Cartilage samples are taken from an individual during or after the treatment of a candidate drug as described herein above. As a comparison, cartilage samples can also taken from either the same individual prior to the treatment of the drug or from another individual not treated with the drug. Nucleic acids are extracted from the samples as described and hybridized to an array of the present invention. If one or more nucleic acid members on the array are found to be expressed at different levels in the sample taken from the treated individual compared to the sample taken from the untreated individual, it was indicative of the efficacy of the drug for the treatment of osteoarthritis. Follow-up analysis (e.g., by PCR or Western blot analysis) can be followed to verify the expression differences.

Variations, modifications, and other implementations of what is described herein will occur to those of ordinary skill in the art without departing from the spirit and scope of the invention. The references provided below and referred to herein above are incorporated herein by reference in their entireties.

---

LENGTHY TABLES

The patent contains a lengthy table section. A copy of the table is available in electronic form from the USPTO web site (http://seqdata.uspto.gov/?pageRequest=docDetail&DocID=US07452667B2). An electronic copy of the table will also be available from the USPTO upon request and payment of the fee set forth in 37 CFR 1.19(b)(3).

---

What is claimed is:

1. A method of diagnosing mild osteoarthritis in a human test individual, said method comprising:
   for each gene of the set of genes consisting of TNFAIP6 and TGFBI,
   (a) determining the level of expression of RNA encoded by said gene in a cartilage sample of said individual; and
   (b) comparing said level with the level of expression of RNA encoded by said gene in control cartilage samples, wherein said control samples are from individuals who have been diagnosed as not having osteoarthritis;

whereby an increase in said level of step (a) relative to said level of expression of said RNA in said control samples is indicative of mild osteoarthritis.

* * * * *